US006936730B1

(12) United States Patent
Ohga et al.

(10) Patent No.: US 6,936,730 B1
(45) Date of Patent: Aug. 30, 2005

(54) PROCESS FOR PRODUCING HYDROGENATED ESTER, HYDROGENATING CATALYST USED THEREFOR AND PROCESS FOR PRODUCING THE CATALYST

(75) Inventors: Kazuhiko Ohga, Oita (JP); Masayuki Fujimoto, Oita (JP); Hiroshi Uchida, Oita (JP); Tsuneo Tajima, Oita (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 09/582,495

(22) PCT Filed: Feb. 21, 2000

(86) PCT No.: PCT/JP00/00977

§ 371 (c)(1),
(2), (4) Date: Jun. 27, 2000

(87) PCT Pub. No.: WO00/64852

PCT Pub. Date: Nov. 2, 2000

Related U.S. Application Data
(60) Provisional application No. 60/141,247, filed on Jun. 30, 1999, provisional application No. 60/147,812, filed on Aug. 10, 1999, and provisional application No. 60/162,896, filed on Nov. 1, 1999.

(30) Foreign Application Priority Data

Apr. 27, 1999  (JP) .......................................... 11-118874
Jul. 7, 1999   (JP) .......................................... 11-193352
Oct. 5, 1999   (JP) .......................................... 11-284520

(51) Int. Cl.$^7$ .............................................. C07C 69/00
(52) U.S. Cl. ................................... 560/128; 560/129
(58) Field of Search ................................ 560/128, 129

(56) References Cited

U.S. PATENT DOCUMENTS 2,476,052 A   7/1949  Lippincott
4,178,314 A  12/1979  Carlock

FOREIGN PATENT DOCUMENTS

| DE | 271985       | 3/1914  |              |
|----|--------------|---------|--------------|
| JP | 55036417 A   | 3/1980  |              |
| JP | 6-279012     | 10/1994 | ...... C01B/31/18 |
| JP | 09194427     | * 7/1997 |              |
| JP | 9-194427 A   | * 7/1997 |              |
| JP | 9-194427     | 7/1997  | ...... C07C/69/02 |
| JP | 10-120605    | 5/1998  | ...... C07C/27/04 |
| JP | 11-47597     | 2/1999  | ...... B01J/23/58 |
| WO | WO 99/64154  | 12/1999 |              |
| WO | WO 00/26175 A1 | 5/2000 |              |

OTHER PUBLICATIONS

Aldrich Catalog, Handbook of Fine Chemicals, 1996–97.*
Jiang, Cuanyu; Zhang, Xiankang; Du, Jianpin; Hua, Jiandong, Fang, Shibi; Jiang, Yingyan, Shanghai Keji Daxue Xuebao (Journal of Shanghai University of Science and Technology), No. 1, pp. 81–87, 1987.*
Russell et al, Journal of Organic Chemistry, vol. 36, No. 14, 1971, pp. 2018–2019.*
Xiangkai et al, Cuiha Xuebao, vol. 17, No. 3, 1996, pp. 260–262.*
International Search Report (foreign language).
Patent Abstract of Japan 09194427 A Jul. 29, 1997.
Patent Abstract of Japan 11047597 A Feb. 23, 1999.
Patent Abstract of Japan 10120605 A May 12, 1998.
Patent Abstract of Japan 06279012 A Oct. 4, 1994.
Young, W., et al. "Allylic Rearrangements. XXX. The Formation and Rearrangement of alpha, alpha–Dialkylally Acetates", J. Am. Chem. Soc., vol. 73, 1951, pp. 780–782.
Lewis, L., "Enhancement of Catalytic Activity through Orthometalation. Synthesis, Structure, and Catalytic Activity of a New Orthometalated Ruthenium Complex", J. Am. Chem. Soc., vol. 108, No. 4, 1986, pp. 743–749.
C. Wilcox, et al, "Substituent Effects in [3, 3]–Sigmatropic Rearrangements. Alkyl Group Effects and Transition–State "Syn–Diaxial" Interactions" J. AM. Chem. Soc., vol. 108, No. 21, 1986, pp. 6636–6642.
Database Caplus Online! Chemical Abstract Service, Columbus, Ohio, US; Database accession No. 93: 94821, XP002236887, abstract, JP 55 036417 A (Dainippon Ink and Chemicals, Inc.) Mar. 14, 1980.
Database Crossfire Beilstein Institute zur Förderung der chemischen Wissenschaften; Database accession No. 231215, abstract.
Eun Lee, et al., "8–Endo Cyclization of (Alkoxycarbonyl) methyl Radicals: Radical Ways for Preparation of Eight–Membered–Ring Lactones" J. Am. Chem. Soc. , 1998, pp. 7469–7478, vol. 120, No. 30, XP002262402 Tables 1 and 2.
Rappoport, et al. "Allylic Oxidation of Olefins by Mercuric Acetate" J. Am. Chem. Soc., 1972, pp. 2320–2329, vol. 94, No. 7, XP002262403.
Robert S. BLY, et al., "Unsaturated Neopentyl Compounds, The Acetolysis of 2,2–Dimethyl–3–buten–1–yl and 2,2, 4–Trimethyl 3–penten–1–yl p–Broomobenzenesulfonates." J. Org. Chem., 1965, pp. 10–22, vol. 30, XP002262404.
William J. Bailey et al., Pyrolysis of Esters. VII. Influence of Acid Portion. J. Org. Chem., 1956, pp. 543–546, vol. 21, XP002262405 table I.
Supplemental European Search Report.

* cited by examiner

Primary Examiner—Rita Desai
Assistant Examiner—Hector M. Reyes
(74) Attorney, Agent, or Firm—Sughrue Mion, PLLC

(57) ABSTRACT

A process for producing a hydrogenated ester by hydrogenating an unsaturated group-containing ester having a specific structure by using a hydrogenating catalyst so as to obtain a hydrogenated ester with a high selectivity. It is preferred that the unsaturated group-containing ester as the raw material is diluted with an inert solvent and/or the concentration of carboxylic acid contained in the raw material is made 1 wt. % or less so as to effect a hydrogenation reaction. The hydrogenating catalyst to be used for the above hydrogenation may preferably be one comprising at least one metal selected from Group 8 elements, Group 9 elements, and Group 10 elements in the periodic table according to *Nomenclature of Inorganic Chemistry, Revised Edition*, 1989, *International Union of Pure and Applied Chemistry*, and preferably has an acidity of $1.0 \times 10^{-1}$ mmol/g or less.

18 Claims, 2 Drawing Sheets

PROCESS FOR PRODUCING HYDROGENATED ESTER, HYDROGENATING CATALYST USED THEREFOR AND PROCESS FOR PRODUCING THE CATALYST

This application claims the priorities of applications based on U.S. application Ser. No. 60/141,247 (filed on Jun. 30, 1999), U.S. application Ser. No. 60/147,812 (filed on Aug. 10, 1999) and U.S. application Ser. No. 60/162,896 (filed on Nov. 1, 1999).

TECHNICAL FIELD

The present invention relates to a process for producing a hydrogenated ester based on a hydrogenation of an unsaturated group-containing ester; a catalyst suitably usable for the process, and a process for producing the catalyst.

More specifically, the present invention relates to a process for producing a hydrogenated ester by effecting the hydrogenation of an unsaturated group-containing ester by use of a hydrogenating catalyst so as to produce a hydrogenated ester corresponding to the unsaturated group-containing ester, wherein the amount of the carboxylic acid based on the hydrogenolysis as a side reaction at the time of the hydrogenation reaction can be reduced and the unsaturated group-containing ester can be converted into the corresponding hydrogenated ester as a product with a high conversion (rate) and a high selectivity factor (or yield); a catalyst suitably usable for the process, and a process for producing such a catalyst.

Herein, the term "(corresponding) hydrogenated ester" described in the present specification means an ester which is obtainable by hydrogenating the entirety or a portion of the unsaturated moiety of the unsaturated group-containing ester to be used as a raw material. Accordingly, the term "hydrogenated ester" naturally refers to a generally named "saturated ester". When a plurality of unsaturated groups are present in the unsaturated group-containing ester as the raw material, this term not only includes a product (so-called "saturated ester") which has been obtained by hydrogenating all of the unsaturated groups of the unsaturated group-containing ester, but also includes a product which has been obtained by hydrogenating a portion of the unsaturated groups of the unsaturated group-containing ester and mixtures of those saturated ester(s) and unsaturated ester(s).

For example, when allyl acetate is used as the unsaturated group-containing ester as the raw material, the corresponding hydrogenated ester refers to n-propyl acetate. Further, when 1,3-butadienyl acetate is used as the raw material, the corresponding hydrogenated ester refers to n-butyl acetate, n-1-butenyl acetate, n-2-butenyl acetate, n-3-butenyl acetate, and mixtures of these components.

BACKGROUND ART

Heretofore, n-propyl acetate, isobutyl acetate, n-butyl acetate, etc., as saturated esters have been widely used as dissolving agents, solvents and reaction solvents, and have become industrially important compounds. These saturated esters are generally produced via the esterification based on the condensation of the corresponding alcohol with carboxylic acid. However, in such an esterification reaction system, the equilibrium state of the reaction cannot be shifted toward the product (ester) side, unless water as a by-product is removed to the outside of the system, and therefore it is difficult to obtain industrially advantageous reaction rate and conversion of the raw material.

In order to solve this problem, there have been presented various proposals such as that in KOKAI (Unexamined Patent Publication) No. Hei. 5-194318. However, as described in this KOKAI publication, there is a problem in that a more complicated reaction apparatus and reaction process are required for the process for industrially producing the carboxylic acid ester via the esterification of the alcohol with the carboxylic acid, as compared with those processes using the other reaction systems.

Further, in the esterification reaction based on the condensation of the alcohol with the carboxylic acid, water is inevitably produced in the system. However, the latent heat of vaporization of water is much larger than the latent heats of vaporization of other organic compounds, and therefore there is also a difficulty in that much energy is consumed in separating the water by distillation.

On the other hand, an unsaturated group-containing ester which contains an unsaturated group such as allyl group, methallyl group, and vinyl group at the alcohol site of the ester can be industrially produced, e.g., via the oxidative carboxylation reaction of the corresponding alkene with carboxylic acid, etc.

Particularly, it is well known that an unsaturated group-containing ester can be produced by reacting the corresponding alkene, oxygen and carboxylic acid in a gas phase in the presence of a palladium catalyst, and there are many known documents concerning such a process. Examples thereof include KOKOKU (Examined Patent Publication) No. Sho. 44-29046, KOKOKU No. Sho. 48-23408, KOKOKU No. Sho. 50-28934, and KOKAI No. Hei. 1-197457. Among these, KOKAI No. Hei. 1-197457 discloses that an unsaturated group-containing ester can be industrially produced at a very high yield and a high space-time yield through the oxidative carboxylation of the corresponding olefin with carboxylic acid.

On the other hand, it is said that an allyl-type ester as one kind of the above-mentioned unsaturated group-containing ester can be industrially produced, e.g., via the above oxidative carboxylation reaction of the corresponding alkene with carboxylic acid, as well as via the reaction of an allyl-type chloride with a carboxylic acid or a carboxylic acid salt, the esterification reaction based on the condensation of an allyl-type alcohol with a carboxylic acid, etc.

Accordingly, various methods, wherein these easily available unsaturated group-containing esters such as allyl-type ester are subjected to a hydrogenation reaction so as to produce a corresponding hydrogenated ester (particularly, saturated ester), have been investigated.

It has heretofore been known that a metal selected from Group 8 elements, Group 9 elements, and Group 10 elements in the periodic table (according to Nomenclature of Inorganic Chemistry, Revised Edition, 1989, International Union of Pure and Applied Chemistry; and in the same manner in the description hereinafter) is effective as a hydrogenating catalyst to be used for the hydrogenation reaction of an unsaturated group-containing ester. However, there has been pointed out the hydrogenolysis of the unsaturated group-containing ester as the raw material, as a problem encountered in the method using such a metal-type catalyst. More specifically, it is known that when an allyl-type ester represented by the following formula (1) or an enol-type ester represented by the following formula (2) is hydrogenated in the presence of a catalyst containing a metal selected from Group 8 elements, Group 9 elements, and Group 10 elements to thereby produce a saturated ester, the hydrogenolysis of the unsaturated group-containing ester as the raw material occurs so as to produce the corresponding carboxylic acid and alkane as by-products ("Catalytic Hydrogenation-Applications to Organic Synthesis" (1st edition, 1st printing, issued on Apr. 10th, 1987, Tokyo Kagaku Dojin), page 116 et seq., may be referred to).

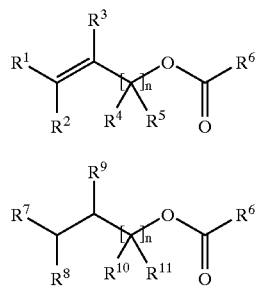

(1)

(2)

As a measure for solving such a problem, there is known a method wherein palladium metal is used as a catalyst in view of the suppression of the hydrogenolysis of the enol-type ester (the above-mentioned "Catalytic Hydrogenation-Application to organic Synthesis", page 116 et seq., may be referred to). Further, there is known a method wherein a rhodium metal is used as a catalyst so as to suppress the hydrogenolysis of an allyl-type ester (W. F. Berkowitz, I. Sasson, P. S. Sampathkumar, J. Hrable, S. C. Choudhry, D. Pierce, Tetrahedron Lett, 1979, page 1641).

However, according to the present inventors' experiments, it has been found that each of the above-mentioned catalysts can effectively suppress the hydrogenolysis with respect to either one of the enol-type ester or the allyl-type ester, but each of the catalysts cannot effectively suppress the hydrogenolysis of both of these unsaturated group-containing esters.

On the other hand, KOKAI NO. Hei. 9-194427 discloses a method for producing a saturated ester from an unsaturated group-containing ester by use of a nickel-type hydrogenating catalyst. According to this patent publication, it is said that this method can effectively suppress the hydrogenolysis by using the nickel-type hydrogenating catalyst, as compared with the method using a palladium metal as a catalyst and the method using a rhodium metal as a catalyst.

However, when the present inventors have tried to practically carry out the hydrogenation reaction according to the above method of the patent publication so as to produce the corresponding saturated ester, it has been found that this process is also accompanied with the decomposition reaction to the corresponding alkane and the corresponding carboxylic acid (i.e., the hydrogenolysis of the raw material), at least to a certain extent.

More specifically, according to the present inventors' experiments, it has been found that even when the above method according to KOKAI No. Hei. 9-194427 is used, it is difficult to conveniently obtain a saturated ester having a high purity reaching the product standard for the saturated esters which are widely used as solvents and reaction solvents. That is, in general, according to the product standard for the saturated esters, the tolerable amount of carboxylic acid to be contained therein corresponds to a concentration of 50 ppm or less, and the purity of the saturated ester is 99.5 mass % or more. In other words, the production of such a carboxylic acid due to the hydrogenolysis reaction poses a very serious problem in view of the product quality of the saturated esters. In addition, it is generally difficult to separate an unsaturated group-containing ester as a raw material (e.g, allyl acetate) and a saturated ester as a product (e.g., n-propyl acetate) from each other by a simple distillation, and therefore a precise multi-stage distillation is required in order to achieve such a product standard.

In view of the foregoing, and in order to simplify the purification step after the completion of the reaction, it is extremely preferred that the conversion of the unsaturated group-containing ester is made 99.8% or more, the selectivity factor for the carboxylic acid produced as a by-product is made as low as possible (the selectivity factor for the carboxylic acid may preferably be 2.0% or less), and the selectivity factor for the hydrogenated ester (particularly, that for the saturated ester) is made higher (the selectivity factor for the saturated ester is made 98.0% or more).

However, for example, the above-mentioned patent publication KOKAI No. Hei. 9-194427 does not describe an En achievement such that when a saturated ester is produced from an unsaturated group-containing ester by use of a nickel-type hydrogenating catalyst, the conversion of the unsaturated group-containing ester is made 99.8% or more, and the selectivity factors for the saturated ester and the carboxylic acid are made 98.0% or more and 2.0% or less, respectively.

An object of the present invention is to provide a process for efficiently producing a hydrogenated ester, wherein the formation of a carboxylic acid due to the hydrogenolysis as a side reaction to the hydrogenation reaction is suppressed when the corresponding hydrogenated ester is produced by the hydrogenation reaction of an unsaturated group-containing ester.

DISCLOSURE OF INVENTION

In order to overcome the above-mentioned problems, the present inventors have performed earnest studies on the hydrogenation reaction of an unsaturated group-containing ester using a hydrogenating catalyst. As a result, the present inventors have found that the unsaturated group-containing ester as the raw material, the concentration of a specific component contained therein, or a specific of parameter for the hydrogenating catalyst has an extremely important effect on the hydrogenolysis reaction.

First, the present inventors have found that the hydrogenation reaction of the unsaturated group-containing ester is conducted along with the dilution thereof with a solvent inert to the reaction, to thereby obtain a hydrogenatedester (particularly, a saturated ester) with a high yield almost without being accompanied by a hydrogenolysis reaction.

The process for producing a hydrogenated ester according to an embodiment of the present invention is based on the above discovery, and more specifically, it is a process for producing a hydrogenated ester by hydrogenating an unsaturated group-containing ester represented by the following general formula (1) in the presence of a hydrogenating catalyst so as to produce a hydrogenated ester corresponding to the unsaturated group-containing ester, wherein the unsaturated group-containing ester is diluted with an inert solvent and a hydrogenation reaction is effected on the unsaturated group-containing ester.

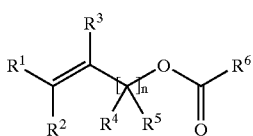

(1)

(wherein $R^1$, $R^2$, $R^3$, $R^4$ and $R^5$ denote an arbitrary alkyl group containing 1–10 carbon atoms, an arbitrary alkenyl group containing 1–10 carbon atoms, or a hydrogen atom and may be the same as or different from each other; the alkyl group and alkenyl group may be either straight-chain or branched; $R^6$ denotes an arbitrary alkyl group which contains 1–10 carbon atoms and may be either straight-chain or branched; and n is 0 or 1.)

The production process according to the present invention having the above-mentioned constitution is based on a present inventors' discovery such that when the prior art hydrogenation reaction as described hereinabove has been conducted practically so as to attempt the production of the corresponding saturated ester, the reaction is also accompanied by the decomposition reaction of the unsaturated group-containing ester into the corresponding alkane and the corresponding carboxylic acid, depending on the concentration of the unsaturated group-containing ester with respect to the reactant liquid containing the unsaturated group-containing ester represented by the general formula (1).

Herein, the "corresponding alkene" described in the present specification means an alkene as a starting material when an unsaturated group-containing ester is formed by an oxidative carboxylation reaction. For example, when the unsaturated group-containing ester is allyl acetate, the corresponding alkene refers to propylene.

Further, the "corresponding alkane" described in the present specification means an alkane which is to be formed by the accompanying hydrogenolysis reaction at the time of the hydrogenation reaction of the unsaturated group-containing ester. For example, when the unsaturated group-containing ester is allyl acetate, the corresponding alkane refers to propane.

Further, the "raw material liquid containing an unsaturated group-containing ester" described in the present specification means the raw material component which has been obtained by excluding hydrogen gas and an inert gas such as nitrogen and alkane, from the liquid and/or gas which contains the unsaturated group-containing ester and is to be charged into a reactor so as to be used for the hydrogenation reaction as the raw material for the reaction step for the corresponding hydrogenated ester.

On the other hand, known publications such as KOKAI No. Hei. 9-194427 do not describe the yield or selectivity factor for the saturated ester particularly corresponding to the concentration of the unsaturated group-containing ester with respect to the raw material liquid, in the case of the hydrogenation reaction of the unsaturated group-containing ester.

The present inventors have also found that a hydrogenolysis reaction is promoted when a carboxylic acid is present so that the concentration thereof contained in the raw material containing an allyl-type ester exceeds a specific value.

More specifically, according to the another embodiment of the present invention, there is provided a process for producing a hydrogenated ester by effecting a hydrogenation reaction on an allyl-type ester represented by the above-mentioned general formula (1) (n=1) by use of a hydrogenating catalyst so as to produce a hydrogenated ester corresponding to the allyl-type ester, wherein the concentration of a carboxylic acid contained in a raw material containing the allyl-type ester represented by the general formula (1) is 1 wt. % or less.

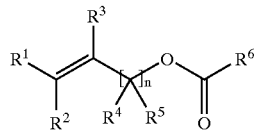

(1)

(wherein $R^1$, $R^2$, $R^3$, $R^4$ and $R^5$ denote a hydrogen atom or an arbitrary alkyl group containing 1–10 carbon atoms and may be the same as or different from each other; the alkyl group may be either straight-chain or branched; and $R^6$ denotes an arbitrary alkyl group which contains 1–10 carbon atoms and may be either straight-chain or branched.)

On the other hand, known publication such as KOKAI No. Hei. 9-194427 do not describe the yield or selectivity factor for the hydrogenated ester particularly corresponding to the amount of the carboxylic acid contained in the raw material containing an allyl-type ester, in the case of the hydrogenation reaction of the allyl-type ester.

The present inventors have further performed earnest studies while directing their attention to a hydrogenating catalyst to be used for the hydrogenation reaction (especially, to various parameters of the catalyst) of an unsaturated group-containing ester. As a result, the present inventors have found that the hydrogenated ester can be produced at a high yield with little decomposition of the unsaturated group-containing ester as a raw material, when a catalyst to be used for hydrogenating an unsaturated group containing ester to produce a corresponding hydrogenated ester contains at least one metal selected from the group consisting of Group 8 elements, Group 9 elements, and Group 10 elements in the periodic table and has an acidity of $1.0 \times 10^{-1}$ mmol/g or less as measured by an ammonia-Temperature Programmed Desorption method (hereinafter referred to as "TDP method").

The hydrogenating catalyst according to a further embodiment of the present invention is a hydrogenating catalyst to be used for hydrogenating an unsaturated group-containing ester represented by the following formula (1) to thereby produce a hydrogenated ester represented by the following formula (2), which contains at least one metal selected from the group consisting of Group 8 elements, Group 9 elements, and Group 10 elements in the periodic table and has an acidity of $1.0 \times 10^{-1}$ mmol/g or less.

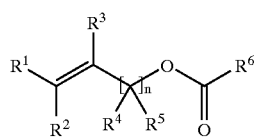

(1)

(wherein n represents 0 or 1, each of $R^1$, $R^2$, $R^3$, $R^4$ and $R^5$ represents a $C_1$–$C_{10}$ alkyl group, a $C_1$–$C_{10}$ alkenyl group, or a hydrogen atom independently from each other, and $R^6$ represents an arbitrary $C_1$–$C_{10}$ alkyl group.)

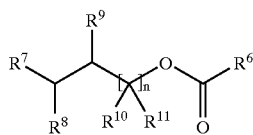

(2)

(wherein n represents 0 or 1, $R^6$ represents an arbitrary $C_1$–$C_{10}$ alkyl group, and each of $R^7$, $R^8$, $R^9$, $R^{10}$ and $R^{11}$ represents a $C_1$–$C_{10}$ alkyl group, a $C_1$–$C_{10}$ alkenyl group, or a hydrogen atom independently from each other.)

Heretofore, it has not been known that the acidity of such a hydrogenating catalyst containing at least one metal selected from the group consisting of Group 8 elements, Group 9 elements, and Group 10 elements in the periodic table is lowered so as to effectively suppress both of the hydrogenolysis reactions to be caused at the time of the hydrogenation reaction in the case of an enol-type ester and in the case of an allyl-type ester, and to enable the hydrogenation reaction thereof at a high selectivity factor.

The present invention further provides a process for producing the above hydrogenating catalyst, which comprises the following first and second steps:

(First Step)

A step for causing a metal compound to be carried on a carrier having an acidity of $1.0 \times 10^{-1}$ mmol/g or less, to thereby obtain a carrier carrying the metal compound; and (Second Step)

A step for reducing the metal compound of the metal compound-carrying carrier obtained in the first step, to thereby obtain a hydrogenating catalyst.

The present invention further provides a process, for producing a hydrogenated ester, which comprises hydrogenating an unsaturated group-containing ester represented by the formula (1) to thereby produce a hydrogenated ester represented by the formula (2), by use of the above-mentioned hydrogenating catalyst.

Figure 1:
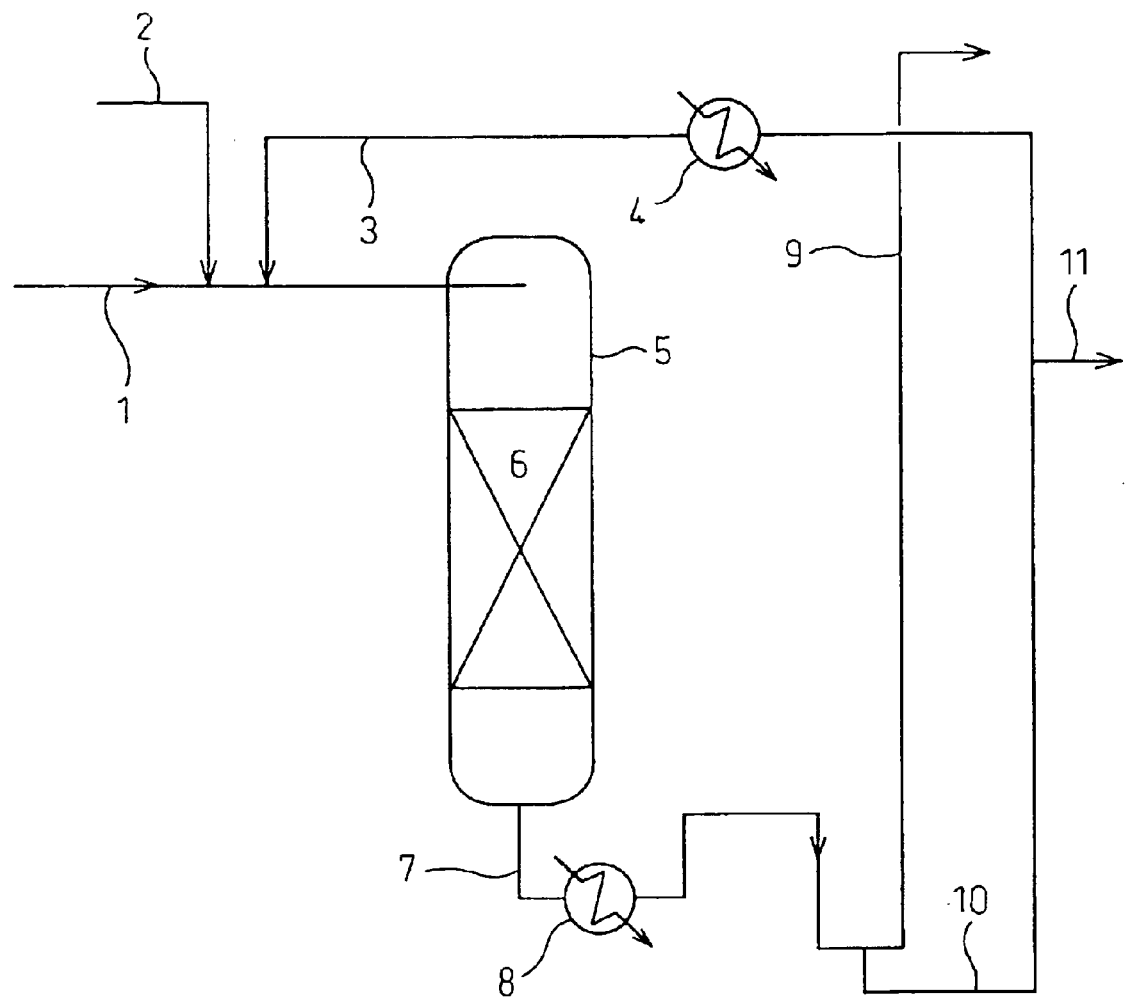
FIG. 1 is a flow sheet showing an embodiment of the apparatus system for practicing the process for producing a hydrogenated ester according to the present invention.

In the drawings, the respective reference numerals have the following meanings.

1: Unsaturated group-containing ester-feeding pipe,
2: Hydrogen gas-feeding pipe,
3: Feed pipe for recycling hydrogenated ester,
4: Heater,
5: Reactor,
6: Layer packed with catalyst,
7: Pipe for taking-out liquid after reactor circulation,
8: Cooler,
9: Pipe for flushing gas,
10: Product liquid-circulating pipe,
11: Pipe for taking-out product liquid,
21: Pipe for charging ion exchange resin,
22: Ion exchange resin tower,
23: Ion exchange resin layer,
24: Pipe for discharging ion exchange resin,
25: Pipe for charging distillation tower,
26: Distillation tower,
27: Pipe for discharging tower bottom liquid from distillation tower, and
28: Pipe for discharging tower top liquid from distillation tower.

BEST MODE FOR CARRYING OUT THE INVENTION

Hereinbelow, the present invention will be described in detail with reference to the accompanying drawings. In the following description, "%" and "part(s)" representing a quantitative proportion or ratio are those based on weight (or mass), unless otherwise noted specifically.

In the process for producing a hydrogenated ester according to the present invention, an unsaturated group-containing ester represented by the following general formula (1) is hydrogenated in the presence of a hydrogenating catalyst so as to produce a hydrogenated ester corresponding to the unsaturated group-containing ester. By this process, e.g., a hydrogenated ester represented by the following general formula (2) may be obtained.

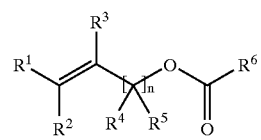

(1)

(wherein $R^1$, $R^2$, $R^3$, $R^4$ and $R^5$ denote an arbitrary alkyl group containing 1–10 carbon atoms, an arbitrary alkenyl group containing 1–10 carbon atoms, or a hydrogen atom and may be the same as or different from each other; the alkyl group and alkenyl group may be either straight-chain or branched; $R^6$ denotes an arbitrary alkyl group which contains 1–10 carbon atoms and may be either straight-chain or branched; and n is 0 or 1.)

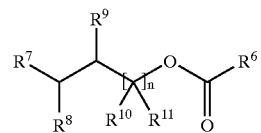

(2)

(wherein n represents 0 or 1, $R^6$ represents an arbitrary $C_1$–$C_{10}$ alkyl group, and each of $R^7$, $R^8$, $R^9$, $R^{10}$ and $R^{11}$ represents a $C_1$–$C_{10}$ alkyl group, a $C_1$–$C_{10}$ alkenyl group, or a hydrogen atom independently from each other.) Specific examples of unsaturated group-containing ester Specific examples of the unsaturated group-containing ester represented by the general formula (1) (corresponding to n=1) which are preferably usable in the present invention may include: an allyl ester wherein n=1 and all of $R^1$, $R^2$, $R^3$, $R^4$, and $R^5$ are hydrogen atoms; a methallyl ester wherein n=1, $R^3$ is a methyl group, and all of $R^1$, $R^2$, $R^4$ and $R^5$ are hydrogen atoms; and a crotyl ester wherein n=1, $R^1$ is a methyl group, and all of $R^2$, $R^3$, $R^4$ and $R^5$ are hydrogen atoms. Further, specific examples of the unsaturated group-containing ester represented by the general formula (1) (corresponding to n=0) may include: a vinyl ester wherein n=0 and all of $R^1$, $R^2$, and $R^3$ are hydrogen atoms; and 1,3-butadienyl ester wherein n=0, $R^1$ is a vinyl group, and all of $R^2$ and $R^3$ are hydrogen atoms; and 1-methyl-1-propenyl esters wherein n=0, both $R^1$ and $R^3$ are methyl groups and $R^2$ is a hydrogen atom. However, the esters to be preferably used in the present invention are not limited to these specific examples.

Preferred specific examples of the above-mentioned unsaturated group-containing ester may include: allyl acetate, allyl propionate, methallyl acetate, methallyl propionate, crotyl acetate, crotyl propionate, vinyl acetate, vinyl propionate, 1,3-butadienyl acetate, 1,3-butadienyl propionate, etc. Particularly preferred examples thereof may include: allyl acetate, methallyl acetate, crotyl acetate, and 1,3-butadienyl acetate.

In an embodiment wherein a hydrogenating catalyst having an acidity of $1.0 \times 10^{-1}$ mmol/g or less is used in combination, it is preferred to use, as specific examples of the above unsaturated group-containing ester (1) (n=1), allyl acetate, allyl propionate, methallyl acetate, methallyl propionate, crotyl acetate, crotyl propionate, etc., and particularly preferably, allyl acetate, methallyl acetate, crotyl acetate, etc. Further, it is preferred to use, as specific examples of the unsaturated group-containing ester represented by the general formula (1) wherein n=0, vinyl acetate, vinyl propionate, 1,3-butadienyl acetate, 1,3-butadienyl propionate, 1-methyl-1-propenyl acetate, 1-methyl-1-propenyl propionate, etc., and particularly preferably, 1,3-butadienyl acetate, 1-methyl-1-propenyl acetate, etc.

In an embodiment of the present invention wherein the unsaturated group-containing ester is an allyl-type ester (n=1), and the concentration of a carboxylic acid contained in a raw material containing the allyl-type ester is 1 mass % or less, specific examples of the preferred allyl-type ester to be used in the present invention may include: an allylic ester wherein all of $R^1$, $R^2$, $R^3$, $R^4$, and $R^5$ are hydrogen atoms, a methallyl ester wherein $R^3$ is a methyl group, and all of $R^1$, $R^2$, $R^4$ and $R^5$ are hydrogen atoms, and a crotyl ester wherein $R^1$ is a methyl group, and all of $R^2$, $R^3$, $R^4$ and $R^5$ are hydrogen atoms. More specific examples thereof may include: allyl acetate, allyl propionate, methallyl acetate, methallyl propionate, crotyl acetate, crotyl propionate, etc. Particularly preferred examples thereof may include allyl acetate, and methallyl acetate.

The term "raw material containing allyl-type ester" in the present specification means the raw material component which has been obtained by excluding hydrogen gas and an inert gas such as nitrogen and alkane, from the liquid and/or gas which contains the allyl-type ester and is to be charged into a reactor so as to be used for the hydrogenation reaction as the raw material for the reaction step for synthesizing the corresponding hydrogenated ester. The term "concentration of carboxylic acid contained in raw material containing allyl-type ester" means the concentration of the carboxylic acid with respect to the raw material component which has been obtained by excluding hydrogen gas and an inert gas such as nitrogen and alkane, from the liquid and/or gas which contains the allyl-type ester. For example, when the liquid to be charged into the reactor is a liquid mixture comprising allyl acetate: n-propyl acetate=1:10 (wt/wt), the "raw material containing allyl-type ester" means the liquid mixture comprising allyl acetate: n-propyl acetate 1:10 (wt/wt), and the concentration of the carboxylic acid in this case is that for the liquid mixture comprising allyl acetate: n-propyl acetate 1:10 (wt/wt).

In the present invention, the method for determining the mixing ratio in a composition may preferably be conducted by an internal standard method for gas chromatography as described hereinafter.

Specific Examples of Hydrogenated Ester

Specific examples of the ester as a product represented by the general formula (2) (corresponding to n=1) may include: n-propyl acetate produced by the hydrogenation of allyl acetate; n-propyl propionate produced by the hydrogenation of allyl propionate; isobutyl acetate produced by the hydrogenation of methallyl acetate; isobutyl propionate produced by the hydrogenation of methallyl propionate; n-butyl acetate produced by the hydrogenation of crotyl acetate; and n-butyl propionate produced by the hydrogenation of crotyl propionate, etc. However, the esters as the products in the present invention are not limited to these specific examples.

Similarly, specific examples of the ester as a product represented by the formula (2) (corresponding to n=0) may include: ethyl acetate produced by the hydrogenation of vinyl acetate; ethyl propionate produced by the hydrogenation of vinyl propionate; n-butyl acetate, 3-butenyl acetate, and mixtures thereof produced by the hydrogenation of 1,3-butadienyl acetate; n-butyl propionate, 3-butenyl propionate, and mixtures thereof produced by the hydrogenation of 1,3-butadienyl propionate; sec-butyl acetate produced by the hydrogenation of 1-methyl-1-propenyl acetate; sec-butyl propionate produced by the hydrogenation of 1-methyl-1-propenyl propionate, etc. However, the esters as the products in the present invention are not limited to these specific examples.

Process for Producing Unsaturated Group-containing Ester

In general, an unsaturated group-containing ester such as allyl-type ester may be industrially produced by either of the following three methods. Herein, the process for producing the unsaturated group-containing ester will be described with reference to that for the allyl-type ester as an embodiment thereof (That is, in the interpretation of this description of the production process, the "allyl-type ester" may be extended so as to include the "unsaturated group-containing ester" unless such an interpretation becomes contrary to the spirit of the corresponding description.)

Thus, the first method is a method wherein a gas mixture comprising the corresponding alkene, oxygen and carboxylic acid are reacted in a gas phase in the presence of a palladium catalyst; the second method is a method wherein an allyl-type chloride is reacted with a carboxylic acid or a salt of carboxylic acid; and the third method is a method wherein the allyl-type ester is produced by an esterification reaction based on the condensation of an allyl-type alcohol with a carboxylic acid.

The allyl-type ester to be used for the raw material in the present invention may be any of those produced by the above-mentioned first to third methods.

However, in the allyl-type ester produced by the above-mentioned second method, in some cases, not only the carboxylic acid but also hydrochloric acid can be produced as acid components, and further a chlorine-containing compound can sometimes be a factor in lowering the activity of the hydrogenating catalyst.

Further, when the allyl-type ester is produced by the above-mentioned third method, the equilibrium state of the reaction cannot be shifted toward the product (allyl-type ester) side unless water as a by-product is removed to the outside of the system, and therefore it is difficult to obtain industrially advantageous reaction rate and conversion of the raw material. Therefore, more complicated reaction apparatus and reaction steps are required for the industrial process for producing the carboxylic acid ester via the esterification reaction, as compared with those for the processes via the other reaction systems, and much energy tends to be consumed in separating the water by distillation.

In consideration of these points, in the process for producing a hydrogenated ester according to the present invention, it is advantageous to use an allyl-type ester which can be produced industrially at a low cost by causing a gas mixture comprising a corresponding alkene, oxygen and a carboxylic acid to react in a gas phase in the presence of a palladium catalyst (the first method).

Raw Material Gas

In the process for producing the hydrogenated ester according to the present invention, a gas comprising at least hydrogen is used as the gas to be supplied to the reaction system, and it is also possible to use nitrogen or a rare gas as a diluting gas, as desired, in addition to hydrogen.

When the process for producing the hydrogenated ester according to the present invention is practiced, the hydrogen gas to be usable therein is not particularly limited. Commercially available hydrogen gas may sufficiently be used as usual, but a gas having a high purity may generally preferably be used. Further, the amount of the hydrogen gas to be supplied may preferably be not less than the amount thereof which is theoretically required for producing the hydrogenated ester (e.g., saturated ester) from the unsaturated group-containing ester. The amount may preferably be in the range of 1.1 times to 3.0 times the theoretically required amount, and more preferably in the range of 1.1 times to 2.0 times the theoretically required amount. When the amount of the hydrogen gas is equal to or less than the theoretically required amount thereof, there is a tendency that when a side reaction such as hydrogenolysis reaction occurs, the amount of hydrogen for the proper reaction becomes smaller than the required amount thereof by the amount of hydrogen consumed by the side reaction. On the other band, an extremely large amount (e.g., an amount exceeding 10.0 times the theoretical amount) of the hydrogen gas to be supplied tends to be unfavorable from an economical point of view.

Hydrogenating Catalyst

As the catalyst to be used in producing the corresponding hydrogenated ester from the unsaturated group-containing ester according to the present invention, it is preferred to use a catalyst comprising an element selected from Group 8 elements, Group 9 elements, or Group 10 elements of the periodic table (according to Nomenclature of Inorganic Chemistry, Revised Edition, 1989, International Union of Pure and Applied Chemistry; the same in the description appearing hereinafter). Specific examples of the element selected from Group 8 elements, Group 9 elements and Group 10 elements of the periodic table may include, e.g., iron, ruthenium, osmium, cobalt, rhodium, iridium, nickel, palladium and platinum. Preferred examples of the element may include palladium, rhodium, ruthenium, and nickel. Among them, palladium, rhodium, and rhuthenium are preferred.

As the raw material compound containing the metal component selected from these Group 8 elements, Group 9 elements and Group 10 elements of the periodic table, it is general to use a salt of a mineral acid such as nitric acid, sulfuric acid, and hydrochloric acid, but it is also possible to use a salt of an organic acid such as acetic acid, a hydroxide, an oxide or a complex salt.

As specific examples of the metal component, specific examples of the iron compound may include: inorganic compounds such as $FeCl_2$, $FeCl_3$, $Fe(NO_3)_3$, $FeSO_4$, and $Fe_2(SO_4)_3$; and organic compounds such as $Fe(CH_3CHOHCOO)_2$, and $Fe(CH_3COCHCOCH_3)_3$. Specific examples of the ruthenium compound may include: inorganic compounds such as $RuCl_3$, organic compounds such as $Ru(CH_3COCHCOCH_3)_3$, and coordination compounds such as pentaammine ruthenium chloride, and triruthenium dodecacarbonyl. Specific examples of the osmium compound may include: inorganic compounds such as $OsCl_3$. Specific examples of the cobalt compound may include: inorganic compounds such as $CoCl_2$, $CO(NO_3)_2$, and $COSO_4$; organic compounds such as $Co(CH_3COO)_2$, $Co(CH_3COCHCOCH_3)_2$, and $Co(CH_3COCHCOCH_3)_3$.

Specific examples of the rhodium compound may include: inorganic compounds such as RhCl3, $Rh(NO_3)_3$, and $Rh_2(SO_4)_3$; organic compounds such as $Rh(CH_3COCHCOCH_3)_3$; and coordination compounds such as tetrarhodium (III) dodecacarbonyl. Specific examples of the iridium compound may include: inorganic compounds such as $IrCl_3$, and $IrCl_4$. Specific examples of the nickel compound may include: inorganic compounds such as $NiCl_2$, and $NiSO_4$; organic compounds such as $Ni(CH_3COO)_2$, and $Ni(CH_3COCHCOCH_3)_2$.

Specific examples of the palladium compound may include: inorganic compounds such as $PdCl_2$, $Pd(NO_3)_2$, $Pd_2SO_4$, and $Na_2PdCl_4$; organic compounds such as $Pd(CH_3COO)_2$, and $Pd(CH_3COCHCOCH_3)_2$; and coordination compounds such as tetraammine palladium (II) chloride. Specific examples of the platinum compound may include: inorganic compounds such as $K_2PtCl_4$, and $PtCl_2$; and organic compounds such as $Pt(CH_3COCHCOCH_3)_2$.

Among the catalysts carried on a carrier, it is particularly preferred to use an element (or a compound containing such an element) which is selected from the Group 8 elements, Group 9 elements, and Group 10 elements of the periodic table, and is carried on an alumina carrier. The element selected from the Group 8 elements, Group 9 elements, and Group 10 elements of the periodic table may particularly preferably be palladium, rhodium, or rhuthenium.

The hydrogenating catalyst to be used in producing the corresponding hydrogenated ester from the unsaturated group-containing ester according to the present invention may be used as an element (or compound) singly or as an element or compound carried on a carrier as desired. For example, in view of the provision of a large metal surface area in the step wherein the hydrogenating catalyst and the unsaturated group-containing ester are contacted each other in the case of a fixed bed-type reactor, it is preferred to use a catalyst carried on a carrier.

Among the catalysts carried on a carrier, it is particularly preferred to use an element (or a compound containing such an element) which is selected from the Group VIII elements, Group IX elements, and Group X elements of the periodic table, and is carried on an alumina carrier. The element selected from the Group VIII elements, Group IX elements, and Group X elements of the periodic table may particularly preferably be palladium, rhodium, or ruthenium.

Acidity of Catalyst

In the process for producing the hydrogenated ester according to the present invention, in view of more effective suppression of the hydrogenolysis reaction, in the catalyst containing an element selected from the Group 8 elements, Group 9 elements and Group 10 elements of the periodic table, the catalyst may preferably have an acidity of $1.0 \times 10^{-1}$ mmol/g or less in terms of the acidity which has been measured by the ammonia-Temperature Programmed Desorption method (hereinafter abbreviated as "TPD method").

The hydrogenating catalyst having the above-mentioned specific acidity may preferably contain at least one metal selected from Group 8 elements, Group 9 elements, and Group 10 elements in the periodic table. Specific examples of the metal may include: iron, rhuthenium, and osmium, which are Group elements, cobalt, rhodium and irridium, which are Group 9 elements; and nickel, palladium, and platinum, which are Group 10 elements, but the metal is not limited to these examples. Preferably, the metal is at least one metal selected from pallidium, rhodium, and ruthenium.

When a hydrogenating catalyst having an acidity of more than $1.0 \times 10^{-1}$ mmol/g is used, the selectivity factor for a corresponding carboxylic acid produced by the hydrogenolysis of an unsaturated group-containing ester represented by the following formula (1) as the raw material may become higher. The hydrogenating catalyst may more preferably have an acidity of $0.5 \times 10^{-1}$ mmol/g or less, particularly preferably $0.3 \times 10^{-1}$ mmol/g or less.

The theoretical interpretation of the relationship between the acidity of the catalyst, and the ease of occurrence of the hydrogenolysis reaction is not fully elucidated at the present stage but, according to the present inventors' investigation, it is presumed that when a hydrogenolysis reaction occurs on a catalyst, the reaction proceeds predominantly by either one of, or in parallel by two or more kinds of, the mechanisms selected from: a radical cleavage reaction on the catalyst, an $S_N1$-type ionic reaction, an $S_Ni$-type reaction or an $S_N2$-type reaction. In this case, according to the present inventors' investigation, it is also presumed that, when a catalyst having a larger acidity acid is present, the acid thereof is adsorbed or attached to the oxygen of the unsaturated group-containing ester, so that the resultant electron density in the C—O bond between the terminal carbon of the alkenyl group (the carbon bonded to the oxygen of the ester) and the oxygen of the ester is decreased and, as a result, any of the radical cleavage reaction, $S_Ni$-type reaction and $S_N2$-type reaction are liable to occur, and the ratio of the hydrogenolysis is also increased.

(Ammonia-TP Method)

In the present invention, the acidity in the catalyst may preferably be measured by the ammonia-TPD method. The ammonia-TPD method will be described in the following.

In this method, at first, ammonia molecules are caused to be adsorbed to a catalyst, and then the ammonia is desorbed therefrom by an increase in temperature. At this time, in a case where plural adsorbed species have adsorption bondings with different strengths and are irreversibly adsorbed, when the temperature of the catalyst is gradually raised, the adsorbed species are sequentially desorbed from the surface of the catalyst, in sequence, from the adsorbed species which has been attached to the surface with a weaker bond. When the difference between the respective adsorption bond strengths is sufficiently large, such an elimination reaction occurs in different temperature regions, and the respective adsorbed species may be distinguished from each other under the condition that the re-adsorption of the desorbed molecules does not occur. In the present invention, it is preferred to analyze the elimination process based on such a principle (with respect to the details, the ammonia-TPD method is described in a journal named "SHOKUBAI (Catalyst)" (edited by the Catalyst Society, Vol. 24, No. 3, pages 226 to 230, issued on Jun. 30, 1982). In the determination of the acidity described in this specification, a vacuum evacuation-type TPD apparatus may preferably be used.

The value of the acidity as used in this specification is that obtained by the following procedure: the number of ammonia molecules which are desorbed in a temperature range of 230–600° C. are measured under the measurement conditions as described below in Examples, and the number is divided by the amount of a sample used which is to be measured.

The hydrogenating catalyst having the above-mentioned specific acidity may preferably contain at least one metal selected from Group 8 elements, Group 9 elements, and Group 10 elements in the periodic table. Specific examples of the metal may include: iron, rhuthenium, and osmium, which are Group elements, cobalt, rhodium and irridium, which are Group 9 elements; and nickel, palladium, and platinum, which are Group 10 elements, but the metal is not limited to these examples. Preferably, the metal is at least one metal selected from pallidium, rhodium, and ruthenium.

As described above, in the present invention, the hydrogenating catalyst may also be used in a form wherein the catalyst is carried on a carrier, as desired. The carrier to be used for such a purpose is not particularly restricted as long as it is a substance (such as porous material) which can be used as an ordinary carrier for carrying thereon a catalyst. Preferred specific examples of the carrier may include: silica ($SiO_2$), alumina ($Al_2O_3$), titanium oxide ($TiO_2$), diatomaceous earth, carbon or mixture of these components.

In view of ease in handling, it is advantageous to use an element selected from Group VIII elements, Group IX elements, and Group X elements in the periodic table, which is carried on a shaped carrier. Specific examples of such a shaped carrier may include: e.g., those having various shapes such as a pellet or a sphere as described hereinafter.

The specific surface area of the carrier to be used as desired in the present invention is not particularly limited, but the carrier may preferably have a large specific surface area, in view of ease in the provision of good dispersion of the catalyst metal. More specifically, the carrier may preferably have a specific surface area of 10 $m^2/g$–1,000 $m^2/g$, more preferably 30 $m^2/g$–800 $m^2/g$ (particularly, 50 $m^2/g$–500 $m^2/g$) as measured by the BET method. In the present specification, the term "specific surface area measured by BET method" refers to a specific surface area obtained by use of the adsorption isotherm derived by Brunauer, Emmett, and Teller (with respect to the details of the BET method, e.g., the description in "Jikken Kagaku Koza (Lectures on Experimental Chemistry) No. 7-Surface Chemistry", page 489, et seq., a portion entitled "11·5 Method for determining surface area of catalyst" third edition, third printing, issued on Aug. 10th, 1968, by Maruzen K.K., may be referred to).

The whole pore volume of the carrier is not particularly limited, but the carrier may preferably have a whole pore volume of 0.05 ml/g–6.5 ml/g, more preferably 0.1 ml/g–5.0 ml/g (particularly, 0.5 ml/g–3.0 ml/g). In the present specification, the term "whole pore volume" refers to the amount defined by the whole volume of pores per 1 g of a sample, which is obtained from an adsorption amount at saturated vapor pressure (with respect to the details of the whole pore volume, e.g., the description in "Shokubai Kogaku Koza (Lectures on Catalytic Engineering) No. 4, Basic method for measuring catalyst", page 69, et seq., a portion entitled "1·3·2 Whole pore volume (C), Method for obtaining whole pore volume by adsorption amount at saturated vapor pressure" (first edition, issued on Jul. 30th, 1964, by Chijin Shokan K.K. may be referred to).

Shape of Carrier

The shape of a carrier usable in the present invention is not particularly limited, but may appropriately be selected from known shapes or forms thereof. In view of the uniformity in the reactor internal pressure, the carrier may preferably be a monolithic catalyst carrier having a shape of pellet, sphere, hollow cylinder, spoke wheel, or honeycomb containing parallel flow channels, or a foamed ceramic having an open-type pore system. Among these, in view of ease in the production process therefor, a shape of pellet or sphere can particularly preferably be used.

The carrier to be used in the process for producing the hydrogenating catalyst according to the present invention may preferably be one such that when the catalyst carried on a carrier is stacked on a catalyst layer so as to form a bulk form, the catalyst can be used without causing an extreme decrease in pressure, and the bulk-stacked catalyst has a very large geometric surface area as compared with the whole volume of the bulk-stacked catalyst. From such a viewpoint, more specifically, the catalyst carrier may preferably have an outer size in the range of 0.5 mm–5.0 mm, more preferably in the range of 1.0 mm–4.5 mm.

Process for Producing Hydrogenating Catalyst

The process for producing the hydrogenating catalyst according to the present invention is not particularly limited. In view of ease in the production thereof, the catalyst having the above-mentioned specific acidity may preferably be produced in the following manner. Such a method comprises at least the following first and second steps.

First step; i.e., a step for causing a metal compound to be carried on a carrier having an acidity of $1.0 \times 10^{-1}$ mmol/g or less to thereby obtain a metal compound-carrying carrier, Second step; i.e., a step for reducing the metal compound of the metal compound-carrying carrier obtained in the above first step to thereby obtain a hydrogenating catalyst.

First Step

In the above first step, i.e., a step for causing a metal compound to be carried on a carrier having an acidity of $1.0 \times 10^{-1}$ mmol/g or less to thereby obtain a metal compound-carrying carrier, a metal compound dissolved in a liquid may preferably be used. As the liquid for dissolving the metal compound, it is preferred to use a liquid (e.g., an aqueous liquid) which has a high solubility to the metal compound and can be absorbed into the carrier.

In the present specification, the term "aqueous liquid" refers to a liquid which comprises water as an essential component, and has a homogeneous phase. In view of the solubility of the metal compound, the aqueous liquid may preferably comprise 50% or more of water, more preferably 75% or more of water, based on the total weight of the aqueous liquid. Specific examples of such an aqueous liquid may include: pure water, various types of aqueous solutions (such as acidic aqueous solution, and alkaline aqueous solution), or a liquid mixture of water and another water-soluble solvent (such as mixture of pure water and alcohol), etc.

Method of Carrying Catalyst

In the present invention, the method for causing a metal compound to be carried on a carrier is not particularly limited. However, it is possible to adopt a known method utilizing co-precipitation (with respect to the details of co-precipitation, e.g., the description in "Shokubai Kogaku Koza No. 5, Method for preparing and testing catalyst", page 8, et seq., a portion entitled "1·1·6 Purity of precipitation and co-precipitation" (issued on Sep. 30th, 1965, by Chijin Shokan K.K. may be referred to); a forced carrying method by evaporation or spraying; and an impregnation method (with respect to the details of these methods, e.g., the description in "Catalytic Hydrogenation-Application to Organic Synthesis", page 5, et seq., a portion entitled "1·2·2 Impregnation method", first edition, first printing, issued on Apr. 10th, 1987, by Tokyo Kagaku Dojin may be referred to). Among these, in view of controllability of the state of the metal compound carried on the carrier, it is particularly preferably to use the impregnation method or forced carrying method by spraying.

In addition, it is possible to provide, as desired, a step wherein the metal compound of the metal compound-carrying carrier is insolubilized in the liquid which has been used at the time of the carrying of the catalyst. When such an insolubilizing step is provided, it is possible to obtain an advantage in preventing the elution of the metal compound. The method for insolubilization to be used for such a purpose is not particularly limited, but it is preferred that the metal compound is converted into an oxide or hydroxide, so as to be insolubilized, by the addition of a basic substance such as NaOH, $Wa_2SiO_3$, or $Ba(OH)_2$.

Further, after the metal compound is caused to be carried on a carrier, as desired, the resultant carrier may also be washed with water and dried at 20–250° C. When such a water washing step is provided, it is possible to obtain an advantage such that an excess of a basic substance, etc., may be removed.

Second Step

Subsequently, there will be described the second step; i.e., a step for reducing the metal compound of the metal compound-carrying carrier obtained in the first step to thereby obtain a hydrogenating catalyst.

The treatment to be conducted in the second steps not particularly limited, but may appropriately be selected from known reducing methods. Specific examples of the reducing methods may include: known liquid-phase reduction treatments, e.g., that using a reducing agent such as NaBH, and hydrozine, and known gas-phase reduction treatments, e.g., that utilizing heating under a stream of hydrogen gas. However, the reducing methods are not limited to these examples (with respect to the details of the reducing methods, e.g., KOKAI No. Hei 7-89896 may be referred to).

Carrying Amount

In the present invention, the amount of the metal component selected from the Group 8 elements, Group 9 elements, and Group 10 elements in the periodic table which is to be carried on a carrier is not particularly limited. However, in view of the cost and catalytic activity of the metal selected from Group 8 elements, Group 9 elements, and Group 10 elements in the periodic table, it is preferred to adjust the amount of the metal in the range of 0.01–20 mass %, more preferably 0.1–10 mass %, based on the entire mass of the catalyst.

Dilution with Inert Solvent

In consideration of a fact that the hydrogenolysis reaction may be suppressed more effectively at a lower reaction temperature, and in consideration of an extremely large quantity of exothermic heat accompanying the hydrogenation (for example, the quantity of exothermic heat accompanying the hydrogenation of 1 Kg of allyl acetate is 1607 kJ), when the unsaturated group-containing ester is simply reacted, the hydrogenolysis reaction can be promoted due to a temperature increase based on the exothermic heat in the reaction system. In the present invention, in order to suppress such an extreme temperature increase, the hydrogenation reaction may preferably be conducted by using, as a reactant liquid containing the unsaturated group-containing ester, a material which has been obtained by diluting the unsaturated group-containing ester with a solvent inert to the hydrogenation reaction. Herein, the "inert solvent" refers to a solvent which does not substantially affect the hydrogenation reaction of the unsaturated group-containing ester.

In an embodiment wherein the hydrogenation reaction is conducted by using as a reactant liquid containing the unsaturated group-containing ester, a material which has been obtained by diluting the unsaturated group-containing ester with an inert solvent, the concentration of the unsaturated group-containing ester may preferably be in the range of 1 wt. % to 50 wt. %, more preferably 3 wt. % to 30 wt. %, most preferably in the range of 5 wt. % to 15 wt. %.

When the concentration of the unsaturated group-containing ester is below 1 wt. %, the extreme temperature increase due to the exothermic heat can be sufficiently suppressed, but the concentration of the unsaturated group-containing ester becomes too low, and as a result, the resultant productivity tends to become too low. On the other hand, when the concentration of the unsaturated group-containing ester exceeds 50 wt. %, it becomes difficult to sufficiently suppress the extreme temperature increase due to the exothermic heat, and further, in the case of the adiabatic-type liquid-phase reaction (particularly, adiabatic liquid-phase reaction of gas-liquid two-phase current type), a possibility that the temperature in the reactor cannot be controlled tends to increase (e.g., the temperature in the reactor cannot be controlled in a preferred range of 0° C.–200° C.).

Solvent Inert to Hydrogenation

The solvent inert to the hydrogenation reaction which is to be used in the above embodiment is not particularly limited, but may preferably comprise an organic solvent which has no C=C bond. When a recycled hydrogenated ester which has been formed by the hydrogenation reaction according to the present invention is used as the inert solvent, it is conceivable that there is a case wherein an ester having a C=C bond remains in a portion of the recycled ester. However, it is not particularly problematic as long as such an ester does not substantially hinder the control of the hydrogenation reaction according to the present invention. Also from such a viewpoint, even in the case of the recycled ester, it is preferred to use an ester wherein all of the C=C bond has been hydrogenated, i.e., a so-called saturated ester.

Specific examples of the above-mentioned inert solvent may include: saturated esters such as ethyl acetate, n-propyl acetate, butyl acetate, isopropyl acetate, n-propyl propionate, ethyl propionate, butyl propionate, and isopropyl propionate; hydrocarbons such as cyclohexane, n-hexane, and n-heptane; aromatic hydrocarbons such as benzene and tolueue; ketones such as acetone and methyl ethyl ketone; halogenated hydrocarbons such as carbon tetrachloride, chloroform, methylene chloride, and methyl chloride; ethers such as diethyl ether and di-n-propyl ether; alcohols such as ethanol, n-propanol, isopropanol, n-butanol, and sec-butanol; amides such as N-methyl-2-pyrrolidone and N,N-dimethyl acetamide. In view of low possibility of a hydrogenolysis reaction of the unsaturated group-containing ester, it is preferred to use saturated esters, hydrocarbons, and ketones.

Product

According to the present invention, there may be obtained a hydrogenating catalyst which can suppress the hydrogenolysis reaction at the time of the hydrogenation of the unsaturated group-containing ester. Further, by use of such a catalyst, it is possible to obtain hydrogenated or saturated esters such as ethyl acetate, n-propyl, acetate, isopropyl acetate, n-butyl acetate, isobutyl acetate, sec-butyl acetate, n-propyl propionate, isopropyl propionate, ethyl propionate, n-butyl propionate, isobutyl propionate, and sec-butyl propionate.

Mode of Reaction

In the process for producing a hydrogenated ester according to the present invention, both of a gas-phase reaction and a liquid-phase reaction may be applicable to the mode of reactions thereof.

Gas-phase Reaction

At first, the gas-phase reaction will be described.

In the case of the gas-phase reaction, in view of the structure of a reaction apparatus, a fixed-bed reaction apparatus, a moving-bed reaction apparatus, or a fluidized-bed reaction apparatus, etc., may be used. Among these, the fixed-bed reaction apparatus is generally used (with respect to the details of the reaction apparatus, "Reaction Engineering (Hanno Kogaku)" written by Kenji Hashimoto pages 200–204, published by Baifukan K.K., 1979, may be referred to).

In the case of gas-phase reaction, however, the following may preferably be considered.

In general, the quantity of exothermic heat accompanying the hydrogenation is extremely large (for example, the quantity of exothermic heat accompanying the hydrogenation of 1 Kg of allyl acetate is 1607 KJ). On the other hand, in the case of the gas-phase reaction, a reactant substance is charged into a reactor at a temperature of not lower than the boiling point of the reactant. In this case, when the space time yield is intended to be increased, the temperature in the reactor is elevated so as to exceed a preferred temperature (e.g., 200° C.) due to an increase in the quantity of exothermic heat accompanying the hydrogenation, and there is a fear that the hydrogenolysis reaction can be accelerated. In order to solve such a problem, the space-time yield may be lowered so as to reduce the exothermic heat, or the temperature in the reactor may be controlled by cooling, etc. In view of the foregoing, the liquid-phase reaction is more advantageous in that the reactant may be charged into the reactor at a temperature lower than the boiling point of the reactant and that maintaining the reaction temperature at a preferred temperature (e.g., 200° C.) is easier.

Liquid-phase Reaction

Subsequently, the liquid-phase reaction will be described.

In the case of the liquid-phase reaction, specific examples of the structure of the reaction apparatus may include a fixed bed-type reactor, a fluidized bed-type reactor, a stirring vessel-type reactor, etc., (with respect to the details of such a reaction apparatus, "Industrial Reaction Apparatuses (Kogyo Hanno Sochi)-Selection, Design and Practical Examples" edited by Kenji Hashimoto, published by Baifukan K.K., 1984 may be referred to). Among these, in view of ease in the separation of the catalyst and product after the reaction, the fixed bed-type reactor is particularly preferred. Herein, the fixed bed-type reactor described in the present invention refers to a circulation-reaction apparatus wherein a catalyst is packed into the fixed bed thereof. Specific examples thereof may include those as described in the above "Industrial Reaction Apparatuses-Selection, Design and Practical Examples", pages 4–7.

Since hydrogen gas is used in the process for producing a hydrogenated ester according to the present invention, the type of flow of the fluids in the fixed bed-type reactor is a two-phase type comprising a liquid including the raw material and a gas comprising the hydrogen gas. In the case of the gas-liquid two-phase current type, the systems therefor may be classified into three types inclusive of a gas-liquid counter current-type, a gas-liquid downward co-current (parallel flow)-type, and a gas-liquid upward co-current-type, depending on the types of flows of the gas and liquid as raw materials. In the present invention, any of these types can be used, but in view of the effective contact between the hydrogen and catalyst to be required for the reaction, the gas-liquid downward parallel flow-type is most preferred.

In view of the foregoing, in order to increase space-time yield while suppressing the hydrogenolysis, the most preferred mode of reaction is the liquid-phase reaction of gas-liquid two-phase current, and the type of the flow is the gas-liquid downward parallel flow-type.

In addition, in the case of the liquid-phase reaction of gas-liquid two-phase current, in order to suppress the hydrogenolysis caused by an increase in the temperature attributed to exothermic heat in the reaction system, it is preferred that, as described above, an unsaturated group-containing ester is diluted with an inert solvent, and the resultant diluted liquid is used as the reactant liquid and is subjected to the hydrogenation reaction in an adiabatic liquid-phase reaction system. This is because a measure such as cooling of the reactor is not necessarily required by lowering the concentration of the unsaturated group-containing ester in the reactant liquid.

Reaction Apparatus

The reaction apparatus to be usable in the present invention is not particularly limited. When a gas-liquid downward parallel flow-type reaction is conducted by using a fixed bed-type reactor, it is preferred to use a reactor equipped with a cooling jacket, an adiabatic-type reaction apparatus and a multi-tubular-type reaction apparatus equipped with a cooling jacket, etc. In view of the construction cost for the reactor and the conversion of the unsaturated group-containing ester, etc., the adiabatic-type reaction apparatus is preferred.

Recycling

As described above, in the present invention, it is possible to recycle the corresponding ester (particularly, saturated ester) which has been formed due to the hydrogenation reaction of the unsaturated group-containing ester, as desired. Specific examples of the practical mode of such recycling may include a process as shown in FIG. 1. Of course, the process shown in FIG. 1 is merely an example of the embodiment of the present invention, and the present invention is not limited to this embodiment.

Referring to FIG. 1, the hydrogenated ester discharged from a reactor (5) is passed through a pipe (10) for circulating the product liquid, and is split into a recycling hydrogenated ester feed pipe (3) and a product liquid discharging pipe (11) with an arbitrary splitting ratio. This ratio between the flow rates for the recycling and product liquid discharging is not particularly limited but may arbitrarily be determined depending on the desired concentration of the unsaturated group-containing ester at the inlet of the reactor (5).

Accordingly, when the hydrogenated ester discharged from the reactor (5) is not recycled so as to be used as the inert solvent, it is also possible to take out all of the hydrogenated ester from the product liquid discharging pipe (11). Further, on the contrary, it is also possible to recycle all of the hydrogenated ester discharged from the reactor (5) so as to be used. Furthermore, it is also possible to add another inert solvent from the outside of the reactor as desired.

Reaction Temperature

The reaction temperature in the process for producing the hydrogenated ester according to the present invention is not particularly limited. The reaction temperature in the present invention may suitably be in the range of 0–200° C., particularly in the range of 40° C.–150° C., while such a temperature is somewhat different depending on the kind of the raw material in same cases. When the reaction is conducted below 0° C., a sufficient reaction rate tends not to be obtained. When the reaction temperature exceeds 200° C., the hydrogenolysis tends to be promoted.

Herein, the reaction temperature described in this specification in the case of the production of the corresponding hydrogenated ester from the unsaturated group-containing ester is defined as the temperature at an arbitrary site in the reactor at the time of the hydrogenation reaction. For example, in the case of an adiabatic-type liquid-phase reaction, the quantity of the exothermic heat accompanying the hydrogenation is large, and therefore the temperature of the reactor inlet is very different from the temperature of the reactor outlet. In this case, the above temperature refers to the temperature at one of all sites ranging from the reactor inlet to the reactor outlet.

When an adiabatic-type fixed-bed reactor is used in the present invention, it is preferred to measure the reaction temperature at least at the inlet of the reactor (top portion of the catalyst layer), and at the outlet of the reactor (bottom portion of the catalyst layer), by using a thermometer with a thermocouple as a measuring device.

Reaction Pressure

In the case of the gas-phase reaction, even when the reaction pressure is ambient or ordinary pressure, sufficient activity can be obtained. Therefore, the reaction may preferably be carried out at ambient pressure. However, it is also possible to accelerate the reaction under a pressurized condition, if the degree of the pressurization is such that the allyl-type ester can be vaporized at 200° C. or lower.

On the other hand, in the case of the liquid-phase reaction of gas-liquid two-phase current type, pressurization is generally preferred so as to ensure a certain concentration of dissolved hydrogen. In order to ensure a sufficient hydrogen concentration in the reactor in the case of the gas-liquid two-phase current-type liquid-phase reaction, the flow type of the current of the gas and liquid may preferably be the gas-liquid downward parallel flow-type as described hereinabove.

In the case of the gas-liquid two-phase current-type liquid-phase reaction, the reaction pressure may preferably be in the range of 0.05 MPa to 10 MPa (gauge pressure), more preferably in the range of 0.3 MPa to 5 MPa (gauge pressure). When the pressure is below 0.05 MPa (gauge pressure), the reaction tends to be not fully promoted. On the other hand, when the pressure exceeds 10 MPa (gauge pressure), the selectivity factor for the hydrogenolysis reaction tends to be large.

In order to ensure a sufficient hydrogen concentration in the reactor, the type of the reaction may most preferably be the gas-liquid downward parallel flow-type as described hereinabove.

Embodiment Using Allyl-type Ester as Raw Material

Hereinbelow, there is described in detail a case using allyl acetate as one example of the allyl-type ester as the raw material to be hydrogenated, which has been produced by causing a gas mixture comprising a corresponding alkene, oxygen and a carboxylic acid to react in a gas phase in the presence of a palladium catalyst.

At first, when a gas mixture comprising propylene, oxygen and acetic acid is passed in the presence of a palladium catalyst while causing the gas mixture to be retained in a gas phase so as to produce allyl acetate, and the resultant allyl acetate is hydrogenated to obtain n-propyl acetate, it is considered that the sites from which the liquid containing the allyl acetate to be possibly used as the raw material is taken out are roughly classified into two kinds thereof.

(1) When a gas mixture comprising propylene, oxygen and acetic acid is passed in the presence of palladium while causing the gas mixture to be retained in a gas phase so as to synthesize allyl acetate, the resultant reaction product gas is cooled to be separated into a non-condensed component and a condensed component, and the condensed component as the crude reaction product liquid is distilled to obtain allyl acetate from the top portion of the column. Then, the acetic acid obtained from the bottom portion of the column is recycled as the raw material for allyl acetate, as described hereinbelow. In this case, in order to suppress the evaporation of the allyl acetate in the step of removing the non-condensed component, acetic acid may be caused to fall by use of a scrubber.

(2) When a gas mixture comprising propylene, oxygen and acetic acid is passed in the presence of palladium while causing the gas mixture to be retained in a gas phase so as to synthesize allyl acetate, the resultant reaction product gas is cooled to be separated into a non-condensed component and a condensed component, and the condensed component as the crude reaction product liquid is as such used for the hydrolysis reaction thereof with water to obtain allyl alcohol and acetic acid. In this case, since the hydrolysis reaction is an equilibrium reaction, the allyl acetate remains. Accordingly, the crude reaction product liquid after the hydrolysis reaction is distilled to obtain an azeotropic composition comprising allyl alcohol, allyl acetate and water from the top portion of the column. Then, the acetic acid obtained from bottom portion of the column is recycled as the raw material for allyl acetate, as described hereinbelow. The azeotropic composition comprising allyl alcohol, allyl acetate and water which has been obtained from the top portion of the column is cooled so as to be phase-separated into an oily phase and an aqueous phase, and allyl acetate is obtained from the oily phase.

In either case of the above two methods (1) and (2), the crude reaction product liquid to be distilled contains a large amount of acetic acid mixed-therein, and therefore the acetic acid can be mixed in the resultant allyl acetate as an impurity depending on the operation conditions for the above procedure. As described above, in order to effectively suppress the hydrogenolysis reaction, the concentration of the carboxylic acid in the raw material containing the allyl-type ester (represented by the general formula (1), n=1) is not higher than a certain value thereof.

Carboxylic Acid Concentration in Allyl-type Ester

According to the present inventors' studies, with respect to the relationship between the carboxylic acid concentration in the raw material containing the allyl-type ester, and the selectivity factor for the corresponding carboxylic acid as a by-product from the hydrogenation reaction of the allyl-type ester, it has been found that the selectivity factor for the carboxylic acid based on the hydrogenation reaction becomes higher as the carboxylic acid concentration becomes higher. Further, according to the present inventors' studies, there is a fear such that this increase in the carboxylic acid concentration or the selectivity factor for the carboxylic acid can invite a decrease in the activity of the catalyst for the hydrogenation reaction in some cases.

Based on these findings, in the present invention, in order to suppress the selectivity factor for the carboxylic acid, due to the hydrogenolysis in the hydrogenation reaction of the allyl-type ester, to a lower value, the carboxylic acid concentration in the raw material containing the allyl-type ester may preferably be 1 wt. % or less. The carboxylic acid concentration may more preferably be 0.5 wt. % or less, more preferably 0.3 wt. % or less.

The theoretical interpretation of the relationship between the carboxylic acid concentration in the raw material containing the allyl-type ester, and the eases of occurrence of the hydrogenolysis reaction is not fully elucidated at the present stage, but according to the present inventors' investigation, it is presumed that, when a hydrogenolysis reaction occurs on a catalyst, the reaction proceeds predominantly by either one of, or in parallel by two or more kinds of, the mechanisms selected from: a radical cleavage reaction on the catalyst, an $S_N1$-type ionic reaction, an $S_Ni$-type reaction or an $S_N2$-type reaction. In this case, according to the present inventors' investigation, it is also presumed that, when a larger amount of the carboxylic acid is present in the raw material containing the allyl-type ester, the carboxylic acid is adsorbed or attached to the oxygen of the allyl-type ester, so that the resultant electron density in the C—O bond between the terminal carbon of the alkenyl group (the carbon bonded to the oxygen of the ester) and the oxygen of the ester is decreased, and as a result, all of the radical cleavage reaction, $S_Ni$-type reaction and $S_N2$-type reaction are liable to occur, and the ratio of the hydrogenolysis is also increased.

As the method of decreasing the concentration of the acetic acid in the allyl acetate which is to be obtained by reacting propylene, oxygen and acetic acid in a gas phase in the presence of a palladium catalyst, it is possible to use a method wherein the allyl acetate obtained in the above method (1) or (2) is distilled again so as to remove the acetic acid; a method wherein the allyl acetate is circulated through activated alumina or activated charcoal so as to remove the acetic acid; etc.

Process for Producing Allyl-type Ester

As the catalyst for producing the allyl-type ester, it is possible to use a general palladium catalyst which can produce an allyl-type ester in a gas phase from the corresponding alkene, oxygen, and carboxylic acid. In view of an improvement in the reactivity, it is preferred to use a palladium catalyst to which a carboxylic acid salt of an alkali metal has been added.

The allyl-type ester may preferably be produced in a manner such that a catalyst is packed into an appropriate reactor, and the reaction is conducted at a temperature of 100° C.–300° C., preferably 120° C.–200° C., under a reaction pressure of atmospheric or ordinary pressure to 3.0 KPa (gauge pressure), preferably 0 MPa–1.0 MPa (gauge pressure). With respect to the carboxylic acid to be supplied, only the amount thereof corresponding to that consumed in the use thereof for the allyl-type ester and the amount thereof lost in the process steps may preferably be added newly so as to obtain a desired composition to be charged for the reaction.

At this time, the composition of the raw material gas such as hydrogen may be changed within a wide range, but it is preferred to use a composition outside of the explosive range thereof. Further, it is also possible to use an inert gas such as nitrogen as a gas for diluting the raw material gas, and in addition, a saturated hydrocarbon such as propane may also be present.

As the structure and type of the reaction apparatus to be used for producing the allyl-type ester, it is possible to use a fixed bed-type reactor, a moving bed-type reactor, a fluidized bed-type reactor, etc., (with respect to the details of the reaction apparatus, "Reaction Engineering" written by Kenji Hashimoto, pages 200–204, published by Baifukan K.K., 1979, may be referred to). In view of the purification of the resultant liquid after the reaction, it is advantageous in practical use to adopt a fixed bed-type reactor comprising a corrosion-resistant reaction tube (e.g., reaction tube made of SUS-306) containing the above-mentioned catalyst packed therein.

The hydrolysis reaction of the allyl-type ester can be conducted by a known method using an acid catalyst or an acidic ion-exchange resin.

EXAMPLES

Hereinbelow, the present invention will be described in more detail with reference to Examples and Reference Examples, but the present invention is not limited to these Examples. In the following Examples and Reference Examples, the conversion, selectivity factor and yield ad are defined according to the following formulas.

Conversion (%)={(Number of moles of unsaturated group-containing ester consumed in reaction)/(Number of moles of unsaturated group-containing ester charged into reactor)}×100

Selectivity factor (%)={(Number of moles of hydrogenated ester or by-product produced)/(Number of moles of unsaturated group-containing ester consumed in reaction)}×100

Yield (%)={(Number of moles of hydrogenated ester produced)/(Number of moles of unsaturated group-containing ester charged into reactor)}×100

Each of the mixing ratios of the respective compositions was determined by gas chromatography. The measurement conditions used in this case are as follows.
(GC Conditions)

Apparatus: GC-14B (mfd. by Shimazu Kagaku K.K.)

Detector: Hydrogen flame ionization detector

Measuring method: Internal standard method
(Internal Standard Substance: N-butyl Acetate)

Injection temperature: 220° C.

Temperature increasing conditions: Retention at 40° C. for ten minutes, thereafter temperature increase at a rate of 10° C./minute, and then retention at 150° C. for ten minutes Column used: DB-WAX (mfd. by J&W Co.), inside diameter 0.25 mm, length 3 m.

Example 1A-1
(Dilution of Raw Material with Inert Solvent)

In accordance with the flow chart shown in FIG. 1, 130 ml of a carrier-type palladium catalyst (3 mm-diameter sphere, silica carrier, palladium content 0.5%, specific surface area 300 M²/g, mfd. by NE-Chem Cat K.K.) as a hydrogenating catalyst was packed into a cylinder-type reactor 5 made of stainless steel having an inside diameter of 20 mmφ so as to form a catalyst-packed layer 6, and the pressure in the reactor 5 was adjusted to 2.0 MPa (gauge pressure) by use of hydrogen. From the upper part of the reactor 5, a liquid mixture comprising recycled n-propyl acetate (hydrogenated ester): allyl acetate (unsaturated group-containing ester)= 12.9:1 (wt/wt) was charged thereinto at 40° C. from a feed pipe 1 for feeding the unsaturated group-containing ester and was circulated in the reactor 5 at a rate of 550 ml/hr, and hydrogen was also circulated from a hydrogen gas-feeding pipe 2 in the reactor 5 at a rate of 18.6 Nl/hr (fixed-bed type, gas-liquid downward parallel flow-type). The temperature of the outlet of the reactor 5 (bottom portion of the catalyst layer) was 97.5° C.

As the n-propyl acetate for dilution, a portion of the product was taken out from a taking-out pipe 7, and was supplied from a feed pipe 3 for recycling the hydrogenated ester into the reactor 5 so as to be used therein for recycling by the process flow shown in FIG. 1.

The reaction mixture from the reactor outlet was condensed and was analyzed by using gas chromatography (GC-14B mfd. by Shimazu Kagaku K.K.; Hydrogen flame ionization detector) under the above-mentioned conditions. The thus obtained results are shown in the following Table 1.

TABLE 1

| | Kind of unsaturated group-containing ester used conversion (%) | Kind of hydrogenated ester Selectivity factor (%) | | Kind of carboxylic acid Selectivity factor (%) |
|---|---|---|---|---|
| | | | Yield (%) | |
| Ex. 1A-1 | Allyl acetate 99.8 | n-propyl 99.3 | acetate 99.1 | Actic acid 0.6 |
| Ex. 1A-2 | Allyl acetate 100.0 | n-propyl 99.1 | acetate 99.1 | Actic acid 0.8 |
| Ex. 1A-3 | Methallyl acetate 99.8 | n-propyl 98.8 | acetate 98.6 | Actic acid 1.1 |
| Ex. 1A-4 | Crotyl acetate 100.0 | n-propyl 98.8 | acetate 98.8 | Actic acid 1.1 |
| Ex. 1A-5 | Allyl acetate 100.0 | n-propyl 94.0 | acetate 94.0 | Actic acid 5.9 |
| Ex. 1A-6 | 1,3-butadienyl acetate 100.0 | n-propyl 99.1 | acetate 99.1 | Actic acid 0.8 |
| Ex. 1A-7 | Allyl acetate 100.0 | n-propyl 99.3 | acetate 99.3 | Actic acid 0.6 |
| Ex. 1B-1 | Allyl acetate 100.0 | n-propyl 96.0 | acetate 96.0 | Actic acid 3.9 |
| Ex. 1B-2 | Allyl acetate 100.0 | n-propyl 95.0 | acetate 95.0 | Actic acid 4.9 |
| Ex. 1B-3 | Methallyl acetate 100.0 | n-propyl 93.0 | acetate 93.0 | Actic acid 6.9 |
| Ex. 1B-4 | Crotyl acetate 100.0 | n-propyl 93.0 | acetate 93.0 | Actic acid 6.9 |
| Ex. 1B-5 | Allyl acetate 100.0 | n-propyl 90.0 | acetate 90.0 | Actic acid 9.9 |
| Ex. 1B-6 | 1,3-butadienyl acetate 100.0 | n-propyl 95.0 | acetate 95.0 | Actic acid 4.9 |
| Ex. 1B-7 | Allyl acetate 100.0 | n-propyl 96.0 | acetate 96.0 | Actic acid 3.9 |

Example 1A-2

An unsaturated group-containing ester was hydrogenated in the same manner as in Example 1A-1 except that 130 ml of a carrier-type palladium catalyst (alumina carrier, pellet with diameter of 3 mm×length of 3 mm, palladium content 0.3%, specific surface area 100 m²/g, mfd. by NE-Chem Cat K.K.) was used as the hydrogenating catalyst instead of 130 ml of the carrier-type palladium catalyst (silica carrier, 3 mm-diameter sphere, palladium content 0.5%, specific surface area 300 m$^2$/g, mfd. by NE-Chem Cat K.K.) used in Example 1A-1; and the pressure in the reactor was 0.9 MPa (gauge pressure) instead of 2.0 MPa (gauge pressure) used in Example 1A-1. The temperature of the reactor outlet (bottom portion of the catalyst layer) was 97.5° C.

The reaction mixture from the reactor outlet was condensed and was analyzed by using gas chromatography (GC-14B mfd. by Shimazu Kagaku K.K.; Hydrogen flame ionization detector) under the above-mentioned conditions. The thus obtained results are shown in the above Table 1.

Example 1A-3

An unsaturated group-containing ester was hydrogenated in the same manner as in Example 1A-1 except that 130 ml of a carrier-type ruthenium catalyst (alumina carrier, pellet with diameter of 3 mm×length of 3 mm, ruthenium content 0.5%, specific surface area 100 m$^2$/g, mfd. by NE-Chem Cat K.K.) was used as the hydrogenating catalyst instead of 130 ml of the carrier-type palladium catalyst (silica carrier, 3 mm-diameter sphere, palladium content 0.5%, specific surface area 300 m$^2$/g, mfd. by NE-Chem Cat K.K.) used in Example 1A-1; and a mixture liquid comprising methallyl acetate and isobutyl acetate was used instead of the mixture liquid comprising allyl acetate and n-propyl acetate, respectively, used as the raw material in Example 1A-1. The temperature of the reactor outlet (bottom portion of the catalyst layer) was 95.5° C.

The reaction mixture from the reactor outlet was condensed and was analyzed by using gas chromatography (GC-14B mfd. by Shimazu Kagaku K.K.; Hydrogen flame ionization detector) under the above-mentioned conditions. The thus obtained results are shown in the above Table 1.

Example 1A-4

An unsaturated group-containing ester was hydrogenated in the same manner as in Example 1A-1 except that 130 ml of a carrier-type rhodium catalyst (alumina carrier, pellet with diameter of 3 mm×length of 3 mm, rhodium content 0.5%, specific surface area 100 m$^2$/g, mfd. by NE-Chem Cat K.K.) was used as the catalyst instead of 130 ml of the carrier-type palladium catalyst (silica carrier, 3 mm-diameter sphere, palladium content 0.5%, specific surface area 300 m$^2$/g, mfd. by NE-Chem Cat K.K.) used in Example 1A-1; and a mixture liquid comprising crotyl acetate and n-butyl acetate was used instead of the mixture liquid comprising allyl acetate and n-propyl acetate, respectively, used as the raw material in Example 1A-1. The temperature of the reactor outlet (bottom portion of the catalyst layer) was 95.5° C.

The reaction mixture from the reactor outlet was condensed and was analyzed by using gas chromatography (GC-14B mfd. by Shimazu Kagaku K.K.; Hydrogen flame ionization detector) under the above-mentioned conditions. The thus obtained results are shown in the above Table 1.

Example 1A-5

An unsaturated group-containing ester was hydrogenated in the same manner as in Example 1A-1 except that 130 ml of a Raney-nickel catalyst (Ni content 70%, Al content 30%; trade name: R-222L mfd. by Nikko Rika K.K.) was used as the catalyst instead of 130 ml of the carrier-type palladium catalyst (silica carrier, 3 mm-diameter sphere, palladium content 0.5%, specific surface area 300 m$^2$/g, mfd. by NE-Chem Cat K.K.) used in Example 1A-1; and the pressure in the reactor was 0.9 MPa (gauge pressure) instead of 2.0 MPa (gauge pressure) used in Example 1A-1. The temperature of the reactor outlet (bottom portion of the catalyst layer) was 97.5° C.

The reaction mixture from the reactor outlet was condensed and was analyzed by using gas chromatography (GC-14B mfd. by Shimazu Kagaku K.K.; Hydrogen flame ionization detector) under the above-mentioned conditions. The thus obtained results are shown in the above Table 1.

Example 1A-6

An unsaturated group-containing ester was hydrogenated in the same manner as in Example 1A-1 except that 130 ml of a carrier-type palladium catalyst (alumina carrier, pellet with diameter of 3 mm×length of 3 mm, palladium content 0.3%, specific surface area 100 m$^2$/g,. mfd. by NE-Chem Cat K.K.) was used as the catalyst instead of 130 ml of the carrier-type palladium catalyst (silica carrier, 3 mm-diameter sphere, palladium content 0.5%, specific surface area 300 m$^2$/g, mfd. by NE-Chem Cat K.K.) used in Example 1A-1; and a mixture comprising 1,3-butadienyl acetate: n-butyl acetate=20:1 (wt/wt) was used instead of the mixture comprising allyl acetate: n-propyl acetate=12.9:1 (wt/wt) as the material used in Example 1A-1. The temperature of the reactor outlet (bottom portion of the catalyst layer) was 105° C.

The reaction mixture from the reactor outlet was condensed and was analyzed by using gas chromatography (GC-14B mfd. by Shimazu Kagaku K.K.; Hydrogen flame ionization detector) under the above-mentioned conditions. The thus obtained results are shown in the above Table 1.

Example 1A-7

Preparation of Hydrogenating Catalyst (1)

1.66 g of Na$_2$PdCl$_4$ (mfd. by Tanaka Noble Metal Industry K.K.) which had preliminarily been dissolved in 80 ml of water (Aqueous Solution-A) was introduced into a one-liter flask. To this flask, 200 g of γ-alumina spheres (mfd. by Nikki Universal K.K., trade name: NST-3, acidity 5.6×10$^{-3}$ mmol/g, average diameter 3.2 mm, specific surface 165 m$^2$/g, whole pore volume 0.90 ml/g) were added, so that the entire amount of the Aqueous Solution-A was absorbed into the γ-alumina.

Separately, 2.63 g of Na$_2$SiO$_3$.9H$_2$O was weighed in a beaker and 100 g of pure water was added thereto to effect dissolution so as to prepare Aqueous Solution-B.

The γ-alumina which had absorbed therein Aqueous Solution-A was added to the beaker containing therein the Aqueous Solution-B prepared above, and was left standing at room temperature for 20 hours. Then, 12.9 g of hydrozine mono-hydrate was gradually added to the resultant mixture under stirring at room temperature. The stirring was continued for 4 hours after the addition of the hydrozine mono-hydrate. Thereafter, the catalyst was separated by filtration using a Nutsche funnel, and pure water was circulated through the catalyst at a flow rate of about 60 ml/min for 48 hours by using a glass vessel through which water could be circulated. Then, the catalyst was dried under an air stream at 110° C. for 4 hours to thereby obtain Hydrogenating Catalyst (1).

When the acidity of Hydrogenating Catalyst (1) was analyzed by the Ammonia-TPD method as described below, the acidity thereof was found to be 1.1×10$^{-3}$ mmol/g.

In the following, the measurement conditions for the Ammonia-TPD method are described.

Measuring apparatus: Automatic Temperature-Increase Desorption-Analyzing Apparatus (vacuum evacuation-type) (mfd. by Nihon Bell K.K.)

Preparation of sample to be measured: A sample was finely crushed by using a mortar. 90 mg of the finely crushed sample was weighed and used as the sample for the Ammonia-TPD measurement.

Temperature increasing condition: The sample was dried at 200° C. for 60 minutes, and was cooled at a rate of −10° C./minute so as to provide a temperature of 100° C. and was caused to absorb ammonia at 100° C. for one hour. Then, the temperature was raised at a rate of 10° C./minute to 600° C., and retained as it was for 10 minutes.

Calculation of acidity: The number of the ammonia molecules which had been eliminated from the sample in the temperature range of 230° C.–600° C. was determined by a mass spectrometer. The thus obtained number of the ammonia molecules was divided by,the amount of the sample used for the measurement so as to calculate the acidity.

(Preparation of Hydrogenated Ester)

An unsaturated group-containing ester was hydrogenated in the same manner as in Example 1A-1 except that 130 ml of Hydrogenating Catalyst (1) prepared above was used as the catalyst instead of 130 ml of the carrier-type palladium catalyst (silica carrier, 3 mm-diameter sphere, palladium content 0.5%, specific surface area 300 m$^2$/g, mfd. by NE-Chem Cat K.K.) used in Example 1A-1; and the circulating velocity of hydrogen was 37.2 liter/hr instead of 18.6 liter/hr used in Example 1A-1. The temperature of the reactor outlet (bottom portion of the catalyst layer) was 94° C.

The reaction mixture from the reactor outlet was condensed and was analyzed by using gas chromatography (GC-14B mfd. by Shimazu Kagaku K.K.; Hydrogen flame ionization detector) under the above-mentioned conditions. The thus obtained results are shown in the above Table 1.

Example 1B-1

(Non-dilution of Unsaturated Group-containing Ester)

130 ml of a carrier-type palladium catalyst which was the same kind as that used in Example 1A-1 was packed into a cylinder-type reactor made of stainless steel equipped with a jacket and having an inside diameter of 20 mmφ, the jacket temperature was set to 90.0° C., and the pressure in the reactor was adjusted to 2.0 MPa (gauge pressure) by use of hydrogen. From the upper part of the reactor, allyl acetate was charged thereinto and was circulated at 100° C. at a rate of 300 ml/hr, and hydrogen was also circulated at a rate of 18.6 l/hr, to thereby hydrogenate an unsaturated group-containing ester. The temperature of the reactor outlet (bottom portion of the catalyst layer) was 102° C.

The reaction mixture from the reactor outlet was condensed and was analyzed by using gas chromatography (GC-14B mfd. by Shimazu Kagaku K.K.; Hydrogen flame ionization detector) under the above-mentioned conditions. The thus obtained results are shown in the above Table 1.

Example 1B-2

An unsaturated group-containing ester was hydrogenated in the same manner as in Example 1B-1 except that 130 ml of a carrier-type palladium catalyst, which was the same kind as that used in Example 1A-2, was used as the catalyst instead of 130 ml of the carrier-type palladium catalyst which was the same kind as that used in Example 1A-1; and the pressure in the reactor was 0.9 MPa (gauge pressure) instead of 2.0 MPa (gauge pressure). The temperature of the reactor outlet (bottom portion of the catalyst layer) was 102° C.

The reaction mixture from the reactor outlet was condensed and was analyzed by using gas chromatography (GC-14B mfd. by Shimazu Kagaku K.K.; Hydrogen flame ionization detector) under the above-mentioned conditions. The thus obtained results are shown in the above Table 1.

Example 1B-3

An unsaturated group-containing ester was hydrogenated in the same manner as in Example 1B-1 except that 130 ml of a carrier-type ruthenium catalyst, which was the same kind as that used in Example 1A-3, was used as the catalyst instead of 130 ml of the carrier-type palladium catalyst which was the same kind as that used in Example 1A-1. The temperature of the reactor outlet (bottom portion of the catalyst layer) was 102° C.

The reaction mixture from the reactor outlet was condensed and was analyzed by using gas chromatography (GC-14B mfd. by Shimazu Kagaku K.K.; Hydrogen flame ionization detector) under the above-mentioned conditions. The thus obtained results are shown in the above Table 1.

Example 1B-4

An unsaturated group-containing ester was hydrogenated in the same manner as in Example 1B-1 except that 130 ml of a carrier-type rhodium catalyst which was the same kind as that used in Example 1A-4 was used as the catalyst instead of 130 ml of the carrier-type palladium catalyst which was the same kind as that used in Example 1A-1. The temperature of the reactor outlet (bottom portion of the catalyst layer) was 102° C.

The reaction mixture from the reactor outlet was condensed and was analyzed by using gas chromatography (GC-14B mfd. by Shimazu Kagaku K.K.; Hydrogen flame ionization detector) under the above-mentioned conditions. The thus obtained results are shown in the above Table 1.

Example 1B-5

An unsaturated group-containing ester was hydrogenated in the same manner as in Example 1B-1 except that 130 ml of a Raney-nickel catalyst, which was the same kind as that used in Example 1A-5, was used as the catalyst instead of 130 ml of the carrier-type palladium catalyst which was the same kind as that used in Example 1A-1; and the pressure in the reactor was 0.9 MPa (gauge pressure) instead of 2.0 MPa (gauge pressure). The temperature of the reactor outlet (bottom portion of the catalyst layer) was 102° C.

The reaction mixture from the reactor outlet was condensed and was analyzed by using gas chromatography (GC-14B mfd. by Shimazu Kagaku K.K.; Hydrogen flame ionization detector) under the above-mentioned conditions. The thus obtained results are shown in the above Table 1.

Example 1B-6

An unsaturated group-containing ester was hydrogenated in the same manner as in Example 1B-1 except that 130 ml of a carrier-type palladium catalyst, which was the same kind as that used in Example 1A-6, was used as the catalyst instead of 130 ml of the carrier-type palladium catalyst which was the same kind as that used in Example 1A-1; and a mixture liquid comprising 1,3-butadienyl acetate: n-butyl acetate=20:18 (wt/wt) was used instead of the mixture comprising allyl acetate: n-propyl acetate=12.9:1 (wt/wt). The temperature of the reactor outlet (bottom portion of the catalyst layer) was 102° C.

The reaction mixture from the reactor outlet was condensed and was analyzed by using gas chromatography (GC-14B mfd. by Shimazu Kagaku K.K.; Hydrogen flame ionization detector) under the above-mentioned conditions. The thus obtained results are shown in the above Table 1.

Example 1B-7

An unsaturated group-containing ester was hydrogenated in the same manner as in Example 1B-1 except that 130 ml of the Hydrogenating Catalyst (1) which was the same kind as that used in Example 1A-7 was used as the catalyst instead of 130 ml of the carrier-type palladium catalyst which was the same kind as that used in Example 1A-1; and the circulating velocity of hydrogen was 37.2 liter/hr instead of 18.6 liter/hr. The temperature of the reactor outlet (bottom portion of the catalyst layer) was 102° C.

The reaction mixture from the reactor outlet was condensed and was analyzed by using gas chromatography (GC-14B mfd. by Shimazu Kagaku K.K.; Hydrogen flame ionization detector) under the above-mentioned conditions. The thus obtained results are shown in the above Table 1.

As described above, on the basis of the comparisons between Example 1A-1 and Example 1B-1, Example 1A-2 and Example 1B-2, Example 1A-3 and Example 1B-3, and Example 1A-4 and Example 1B-4, Example 1A-5 and Example 1B-5, Example 1A-6 and Example 1B-6, and Example 1A-7 and Example 1B-7, it is clear that a hydrogenated ester is provided with a high yield almost without being accompanied by a hydrogenolysis reaction, according to an embodiment of the present invention wherein an unsaturated group-containing ester is diluted with an inert solvent.

Example 2A-1

(Production of Hydrogenating Catalyst (3))

$Na_2PdCl$, (1.66 g) (mfd. by Tanaka Noble Metal Industry K.K.) was dissolved in water (190 ml), and the resultant solution (aqueous solution A) was placed in a one-liter flask. To the flask, silica balls (200 g) (Cariact Q-10, mfd. by Fuji Silysia Chemical Ltd.; acidity $1.1 \times 10^{-3}$ mmol/g, average diameter 3 mm; specific surface area 300 $m^2/g$, whole pore volume 1.0 ml/g) were added, to thereby cause the total amount of the aqueous solution A to be absorbed in the silica.

Separately, $Na_2SiO_3.9H_2O$ (2.63 g) was weighed and placed in a beaker, and pure water (100 g) was added to the beaker to effect dissolution, to thereby prepare aqueous solution B.

The silica which had absorbed the aqueous solution A was added to the aqueous solution B placed in the beaker, and the mixture was allowed to stand at room temperature for 20 hours. Subsequently, hydrazine monohydrate was added, and the resultant mixture was stirred for four hours. A formed catalyst was collected through filtration using a Nutsche funnel, and pure water was circulated through the catalyst at a flow rate of about 60 ml/min for 48 hours by using a glass vessel through which water could be circulated. Then, the catalyst was dried under air stream at 110° C. for 4 hours, to thereby obtain hydrogenating catalyst (2).

When the acidity of the hydrogenating catalyst (2) prepared above was analyzed by the above-mentioned In, ammonia-TPD method, the acidity was found to be $1.1 \times 10^{-3}$ mmol/g.

Example 2A-2

Production of Hydrogenating Catalyst (3)

$Na_2PdCl_4$ (1.66 g) (mfd. by Tanaka Noble Metal Industry K.K.) was dissolved in water (80 ml), and the resultant solution (aqueous solution A) was placed in a one-liter flask. To the flask, γ-alumina balls (200 g) (NST-3, mfd. by Nikki-Universal K.K.; acidity $5.6 \times 10^{-3}$ mmol/g, average diameter 3.2 mm, specific surface area 165 $m^2/g$, whole pore volume 0.90 ml/g) were added, to thereby cause the total amount of the aqueous solution A to be absorbed in γ-alumina.

Separately, $Na_2SiO_3.9H_2O$ (2.63 g) was weighed and placed in a beaker, and pure water (100 g) was added to the beaker, to thereby prepare aqueous solution B.

The γ-Alumina which had absorbed aqueous solution A was added to aqueous solution B placed in the beaker, and the mixture was allowed to stand at room temperature for 20 hours. Subsequently, hydrazine monohydrate (12.9 g) was gradually added to the mixture at room temperature with stirring. After addition of hydrazine monohydrate, the resultant mixture was stirred for four hours. A formed catalyst was collected through filtration using a Nutsche funnel, and pure water was circulated through the catalyst at a flow rate of about 60 ml/min for 48 hours by using a glass vessel through which water could be circulated. Then, the catalyst was dried under air stream at 110° C. for 4 hours, to thereby obtain hydrogenating catalyst (3).

When the acidity of the hydrogenating catalyst (3) prepared above was analyzed by the ammonia-TPD method under the same conditions and by the same method as in Example 2A-1, the acidity was found to be $5.6 \times 10^{-3}$ mmol/g.

Example 2A-3

Production of Hydrogenating Catalyst (4)

$Na_2PdCl_4$ (2.765 g) (mfd. by Tanaka Noble Metal Industry K.K.) was dissolved in water (90 ml), and the resultant solution (aqueous solution A) was placed in a one-liter flask. To the flask, γ-alumina balls (200 g) (KHA-24, mfd. by Sumitomo Chemical K.K.; acidity $1.0 \times 10^{-2}$ mmol/g) were added, to thereby cause the total amount of the aqueous solution A to be absorbed in γ-alumina.

Separately, $Na_2SiO_3.9H_2O$ (4.38 g) was weighed and placed in a beaker, and pure water (100 g) was added to the beaker to effect dissolution, to thereby prepare aqueous solution B.

The γ-Alumina which had absorbed aqueous solution A was added to aqueous solution B placed in the beaker, and the mixture was allowed to stand at room temperature for 20 hours. Subsequently, a formed catalyst was collected through filtration, washed with pure water (1 liter×10 times), dried at 70° C. and 10 mmHg (1 mmHg=133.322 Pa), and then reduced in an atmosphere of hydrogen at 200° C. for two hours (conditions for the reduction treatment: pressure 1 MPa (gauge pressure), flow rate of hydrogen 18.6 Nl/hr), to thereby obtain hydrogenating catalyst (4).

When the acidity of the hydrogenating catalyst (4) prepared above was analyzed by the ammonia-TPD method under the same conditions and by the same method as in Example 2A-1, the acidity was found to be $1.0 \times 10^{-2}$ mmol/g.

Example 2A-4

Production of Hydrogenating Catalyst (5)

$RhCl_3.3H_2O$ (2.54 g) (mfd. by Wako Pure Chemical Industries, Ltd.) was dissolved in water (190 ml), and the resultant solution (aqueous solution A) was placed in a one-liter flask. To the flask, silica balls (200 g) (Cariact Q-10, mfd. by Fuji Silysia Chemical Ltd.; acidity $1.1 \times 10^{-3}$ mmol/g, diameter approximately 3 mm, specific surface area 300 m$^2$/g, whole pore volume 1.0 ml/g) were added, to thereby cause the total amount of the aqueous solution A to be absorbed in the silica.

Separately, $Na_2SiO_3 \cdot 9H_2O$ (6.79 g) was weighed and placed in a beaker, and pure water (100 g) was added to the beaker to effect dissolution, to thereby prepare aqueous solution B. The silica which had absorbed aqueous solution A was added to aqueous solution B placed in the beaker, and the mixture was allowed to stand at room temperature for 20 hours. Subsequently, a formed catalyst was collected through filtration, washed with pure water (1 liter×10 times) by using a beaker, dried at 70° C. and 10 mmHg, and then reduced in an atmosphere of hydrogen at 200° C. for two hours (conditions for the reduction treatment: pressure 1 MPa (gauge pressure), flow rate of hydrogen 18 Nl/hr), to thereby obtain hydrogenating catalyst (5).

When the acidity of the hydrogenating catalyst (5) prepared above was analyzed by the ammonia-TPD method under the same conditions and by the same method as in Example 2A-1, the acidity was found to be $1.1 \times 10^{-3}$ mmol/g.

Example 2A-5

Production of Hydrogenating Catalyst (6)

$RhCl_3 \cdot nH_2O$ (n=1–3) (2.41 g) (mfd. by Wako Pure Chemical Industries, Ltd.) was dissolved in water (80 ml), and the resultant solution (aqueous solution A) was placed in a one-liter flask. To the flask, γ-alumina balls (200 g) (trade name: NST-3, mfd. by Nikki-Universal K.K.; acidity $5.6 \times 10^{-3}$ mmol/g, average diameter 3.2 mm, specific surface area 165 m$^2$/g, whole pore volume 0.90 ml/g) were added, to thereby cause the total amount of the aqueous solution A to be absorbed in γ-alumina.

Separately, $Na_2SiO_3 \cdot 9H_2O$ (6.91 g) was weighed and placed in a beaker, and pure water (100 g) was added to the beaker to effect dissolution, to thereby prepare aqueous solution B. The γ-alumina which had absorbed aqueous solution A was added to aqueous solution B placed in the beaker, and the mixture was allowed to stand at room temperature for five hours. Subsequently, hydrazine monohydrate (12.9 g) was gradually added to the mixture at room temperature with stirring. After addition of hydrazine monohydrate, the resultant mixture was stirred for four hours. A formed catalyst was collected through filtration using a Nutsche funnel, and pure water was circulated through the catalyst at a flow rate of about 60 ml/min for 48 hours by using a glass vessel through which water could be circulated. Then, the catalyst was dried under air stream at 110° C. for 4 hours, to thereby obtain hydrogenating catalyst (6).

When the acidity of the hydrogenating catalyst (5) prepared above was analyzed by the ammonia-TPD method under the same conditions and by the same method as in Example 2A-1, the acidity was found to be $6.0 \times 10^{-3}$ mmol/g.

Example 2A-6

Production of Hydrogenated Ester

Referring to FIG. 1, hydrogenating catalyst (2) (130 ml) prepared in Example 2A-1 was charged into a stainless steel cylindrical reactor having an inside diameter of 20 mmφ and the internal pressure of the reactor was controlled to 2.0 MPa (gauge pressure) by hydrogen. From a top portion of the reactor, a recycled mixture containing n-propyl acetate and allyl acetate (12.9:1 (wt/wt)) and having a temperature of 40° C. was caused to be circulated in the reactor at 550 ml/hour. Further, hydrogen was circulated in the reactor at 18.6 Nl/hour. The temperature of the outlet of the reactor (a bottom portion of a catalyst layer) was 94° C.

The reaction mixture from the outlet of the reactor was condensed and analyzed by gas chromatography (by use of GC-14B with a hydrogen-flame ionization detector, mfd. by Shimadzu Kagaku K.K.) under the above-mentioned conditions. The analysis revealed that the conversion of allyl acetate was 99.8%; the selectivity factor for n-propyl acetate was 99.3%; the yield of n-propyl acetate was 99.1%; and the selectivity factor for acetic acid was 0.6%.

Example 2A-7

Production of Hydrogenated Ester

An unsaturated group-containing ester was hydrogenated in the same manner as in Example 2A-6, except that hydrogenating catalyst (3) (130 ml) prepared in Example 2A-2 was used instead of the hydrogenating catalyst (2) (130 ml) prepared in Example 2A-1, and the internal pressure of the reactor was controlled to 0.9 MPa (gauge pressure) instead of the 2.0 MPa (gauge pressure) used in Example 2A-6. The temperature of the outlet of the reactor (a bottom portion of a catalyst layer) was 94° C.

The reaction mixture from the outlet of the reactor was condensed and analyzed by gas chromatography (by use of GC-14B with a hydrogen-flame ionization detector, mfd. by Shimadzu Kagaku K.K.) under the above-mentioned conditions. The analysis revealed that the conversion of allyl acetate was 100.0%; the selectivity factor for n-propyl acetate was 98.6%; the yield of n-propyl acetate was 98.6%; and the selectivity factor for acetic acid was 1.3%.

Example 2A-8

Production of Hydrogenated Ester

An unsaturated group-containing ester was hydrogenated in the same manner as in Example 2A-6, except that hydrogenating catalyst (5) prepared in Example 2A-5 (130 ml) was used instead of hydrogenating catalyst (2) (130 ml) prepared in Example 2A-1. The temperature of the outlet of the reactor (a bottom portion of a catalyst layer) was 94° C.

The reaction mixture from the outlet of the reactor was condensed and analyzed by gas chromatography (by use of GC-14B with a hydrogen-flame ionization detector, mfd. by Shimadzu Kagaku K.K.) under the above-mentioned conditions. The analysis revealed that the conversion of allyl acetate was 99.8%; the selectivity factor for n-propyl acetate was 98.8%; the yield of n-propyl acetate was 98.6%; and the selectivity factor for acetic acid was 1.1%.

Example 2A-9

Production of Hydrogenated Ester

An unsaturated group-containing ester was hydrogenated in the same manner as in Example 2A-6, except that hydrogenating catalyst (5) (130 ml) prepared in Example 2A-4 was used instead of hydrogenating catalyst (2) (130 ml) prepared in Example 2A-1. The temperature of the outlet of the reactor (a bottom portion of a catalyst layer) was 94°0 C.

The reaction mixture from the outlet of the reactor was condensed and analyzed by gas chromatography (by use of GC-14B with a hydrogen-flame ionization detector, mfd. by Shimadzu Kagaku K.K.) under the above-mentioned conditions. The analysis revealed that the conversion of allyl acetate was. 100.0%; the selectivity factor for n-propyl acetate was 98.8%; the yield of n-propyl acetate was 98.8%; and the selectivity factor for acetic acid was 1.1%.

Example 2A-10

Production of Hydrogenated Ester

Referring to FIG. 1, Hydrogenating catalyst (4) (130 ml) prepared in Example 2A-3 was charged into a stainless steel cylindrical reactor equipped with a jacket and having an inside diameter of 20 mmϕ. The jacket temperature was set to 90.0° C. and the internal pressure of the reactor was controlled to 2.0 MPa (gauge pressure) by hydrogen. From a top portion of the reactor, allyl acetate having a temperature of 40° C. and hydrogen were caused to be circulated in the reactor at 300 ml/hour and 18.6 Nl/hour, respectively. The temperature of the outlet of the reactor (a bottom portion of a catalyst layer) was 90.5° C.

The reaction mixture from the outlet of the reactor was condensed and analyzed by gas chromatography (by use of GC-14B with a hydrogen-flame ionization detector, mfd. by Shimadzu Kagaku K.K.) under the above-mentioned conditions. The analysis revealed that the conversion of allyl acetate was 100.0%; the selectivity factor for n-propyl acetate was 98.0%; the yield of n-propyl acetate was 98.0%; and the selectivity factor for acetic acid was 1.9%.

Example 2A-11

Production of Hydrogenated Ester

An unsaturated group-containing ester was hydrogenated in the same manner as in Example 2A-6, except that hydrogenating catalyst (3) (130 ml) prepared in Example 2A-2 was used instead of hydrogenating catalyst (2) (130 ml) prepared in Example 2A-1; 1,3-butadienyl acetate and n-butyl acetate were used for a mixture liquid instead of allyl acetate and n-propyl acetate constituting the mixture liquid used in Example 2A-6, respectively; and the flow rate of hydrogen was changed from 18.6 Nl/hr to 37.2 Nl/hr. The temperature of the outlet of the reactor (a bottom portion of a catalyst layer) was 95.5° C.

The reaction mixture from the outlet of the reactor was condensed and analyzed by gas chromatography (by use of GC-14B with a hydrogen-flame ionization detector, mfd. by Shimadzu Kagaku K.K.) under the above-mentioned conditions. The analysis revealed that the conversion of 1,3-butadienyl acetate was 100.0%; the selectivity factor for n-butyl acetate was 99.1%; the yield of n-butyl acetate was 99.1%; and the selectivity factor for acetic acid was 0.9%.

Example 2B-1

Production of Hydrogenated Ester

Referring to FIG. 1, a stainless steel cylindrical reactor having an inside diameter of 20 mmϕ was charged with a sponge nickel catalyst (trade name: R-200L, mfd. by Nikko Rika K.K., Ni content 70%, Al content 30%) having an acidity, as measured through an ammonia-TPD method under the same conditions employed in Example 2A-6, of $2.0 \times 10^{-1}$ mmol/g (130 ml). The internal pressure of the reactor was controlled to 0.9 MPa (gauge pressure) by hydrogen. From a top portion of the reactor, hydrogen, and a recycled mixture liquid containing n-propyl acetate and allyl acetate (12.9:1 (wt/wt)) and having a temperature of 40° C. were caused to flow into the reactor at 18.6 Nl/hr and 550 ml/hour, respectively. The temperature of the outlet of the reactor (a bottom portion of a catalyst layer) was 95.5° C.

The reaction mixture from the outlet of the reactor was condensed and analyzed by gas chromatography (by use of GC-14B with a hydrogen-flame ionization detector, mfd. by Shimadzu Kagaku K.K.) under the above-mentioned conditions. The analysis revealed that the conversion of allyl acetate was 100.0%; the selectivity factor for n-propyl acetate was 94.0%; the yield of n-propyl acetate was 94.0%; and the selectivity factor for acetic acid was 5.9%.

Example 2B-2

Production of Hydrogenated Ester

Referring to FIG. 1, a stainless steel jacketed cylindrical reactor having an inside diameter of 20 mmϕ was charged with a palladium-on-carrier catalyst (130 ml) (mfd. by Tanaka Noble Metal Industry K.K., alumina carrier, Pd content 5%) having an acidity, as measured through an ammonia-TPD method under the same conditions employed in Example 2A-6, of $2.0 \times 10^{-2}$ mmol/g. The jacket temperature and the internal pressure of the reactor were controlled to 90.0° C. and 2.0 MPa (gauge pressure) by hydrogen, respectively. From a top portion of the reactor, hydrogen and allyl acetate having a temperature of 40° C. were caused to flow into the reactor at 18.6 Nl/hr and 300 ml/hour, respectively. The temperature of the outlet of the reactor (a bottom portion of a catalyst layer) was 90.5° C.

The reaction mixture from the outlet of the reactor was condensed and analyzed by gas chromatography (by use of GC-14B with a hydrogen-flame ionization detector, mfd. by Shimadzu Kagaku K.K.) under the above-mentioned conditions. The analysis revealed that the conversion of allyl acetate was 100.0%; the selectivity factor for n-propyl acetate was 92.0%; the yield of n-propyl acetate was 92.0%; and the selectivity factor for acetic acid was 7.9%.

Example 2B-3

Production of Hydrogenated Ester

Referring to FIG. 1, a stainless steel cylindrical reactor having an inside diameter of 20 mmϕ was charged with a sponge nickel catalyst (130 ml) (R-222L, mfd. by Nikko Rika K.K., Ni content 70%, Al content 30%) having an acidity, as measured through an ammonia-TPD method under the same conditions employed in Example 2A-1, of $2.0 \times 10^{-1}$ mmol/g. The internal pressure of the reactor was controlled to 0.9 MPa (gauge pressure) by hydrogen. From a top portion of the reactor, hydrogen, and a recycled mixture liquid containing n-butyl acetate and 1,3-butadienyl acetate (12.9:1 (wt/wt)) and having a temperature of 40° C. were caused to flow into the reactor at 37.2 Nl/hr and 550 ml/hour, respectively. The temperature of the outlet of the reactor (a bottom portion of a catalyst layer) was 95.5° C.

The reaction mixture from the outlet of the reactor was condensed and analyzed by gas chromatography (by use of GC-14B with a hydrogen-flame ionization detector, mfd. by Shimadzu Kagaku K.K.) under the above-mentioned conditions. The analysis revealed that the conversion of 1,3-butadienyl acetate was 100.0%; the selectivity factor for n-butyl acetate was 94.0%; the yield of n-butyl acetate was 94.0%; and the selectivity factor for acetic acid was 5.9%.

Example 3A-1

One liter of a catalyst having a particle size of 5 mm was obtained through an impregnation method by causing 4.5 g of palladium and 52 g of potassium acetate to be carried on 540 g of silica (surface area 96 m²/g, pore volume 0.78 ml/g, average pore radius 15 mm, bulk density 540 g/l).

One liter of the thus obtained catalyst was packed into a reactor made of stainless steel having a diameter of 27 mm. The gas to be charged thereinto was adjusted so as to provide a gas composition comprising 12 mol % of propylene, 7.5 mol % of oxygen, 9.0 mol % of acetic acid, and 71.5 mol % of a diluting gas, and the gas was supplied onto the catalyst which had been heated to 145° C. so as to provide a space velocity of 1800/hr and to cause a reaction at a reaction pressure of 0.4 MPa (gauge pressure).

The resultant reaction product gas was cooled so as to be separated into a non-condensed component and a condensed component, and the crude reaction product liquid was distilled to obtain the following composition (hereinafter, referred to as "Composition-A") from the top portion of the column.

| Composition-A |
| --- |
| Allyl acetate 97.7 wt. % |
| Allyl alcohol 0.1 wt. % |
| Acetic acid 2.0 wt. % |
| Others 0.2 wt. % |

Tomita-A61, mfd. by Tomita Pharmaceutical K.K.) was packed into a reactor made of glass having a diameter of 100 mm, and the Composition-A was circulated therein so as to provide a space velocity of 1/hr (i.e., 500 ml/hr), to thereby obtain a mixture having the following composition (hereinafter, referred to as "Composition-B").

| Composition-B |
| --- |
| Allyl acetate 99.6 wt. % |
| Allyl alcohol 0.1 wt. % |
| Acetic acid 0.1 wt. % |
| Others 0.2 wt. % |

(Hydrogenation of Unsaturated Group-containing Ester)

Referring to FIG. 1, 130 ml of a carrier-type palladium catalyst (alumina carrier, pellet with diameter of 3 mm×length of 3 mm, palladium content 0.3%, specific surface area 100 m²/g, mfd. by NE-Chem Cat K.K.) was packed into a cylinder-type reactor made of stainless steel equipped with a jacket and having an inside diameter of 20 mmφ, the jacket temperature was set to 90.0° C., and the pressure in the reactor was adjusted to 1.0 MPa (gauge pressure) by use of hydrogen.

From the upper part of the reactor, 10 kg of the Composition-B was charged thereinto and was circulated therein at 40° C. at a rate of 550 ml/hr and hydrogen was also circulated therein at a rate of 18.6 Nl/hr. The temperature of the reactor outlet (bottom portion of the catalyst layer) was 90.5° C.

The reaction mixture from the reactor outlet was condensed to obtain 10 kg of a liquid. The resultant liquid was analyzed by using gas chromatography under the above-mentioned conditions (except that the injection temperature was 200° C.), and it was found that the conversion of allyl acetate was 100.0%, the selectivity factor for n-propyl acetate was 99.2%, the yield of n-propyl acetate was 99.2%, and the selectivity factor for acetic acid was 0.7%.

Example 3A-2

One liter of a catalyst having a particle size of 5 mm was obtained through an impregnation method by causing 4.5 g of palladium and 52 g of potassium acetate to be carried on 540 g of silica (surface area 96 m²/g, pore volume 0.78 ml/g, average pore radius 15 mm, bulk density 540 g/l).

One liter of the thus obtained catalyst was packed into a reactor made of stainless steel having a diameter of 27 mm. The gas to be charged thereinto was adjusted so as to provide a gas composition comprising 12 mol % of propylene, 7.5 mol % of oxygen, 9.0 mol % of acetic acid, and 71.5 mol % of a diluting gas, and the gas was supplied onto the catalyst which had been heated to 145° C. so as to provide a space velocity of 1800/hr and to cause a reaction at a reaction pressure of 0.4 MPa (gauge pressure). In this manner, a reaction product gas mainly comprising allyl acetate was obtained.

Figure 2:
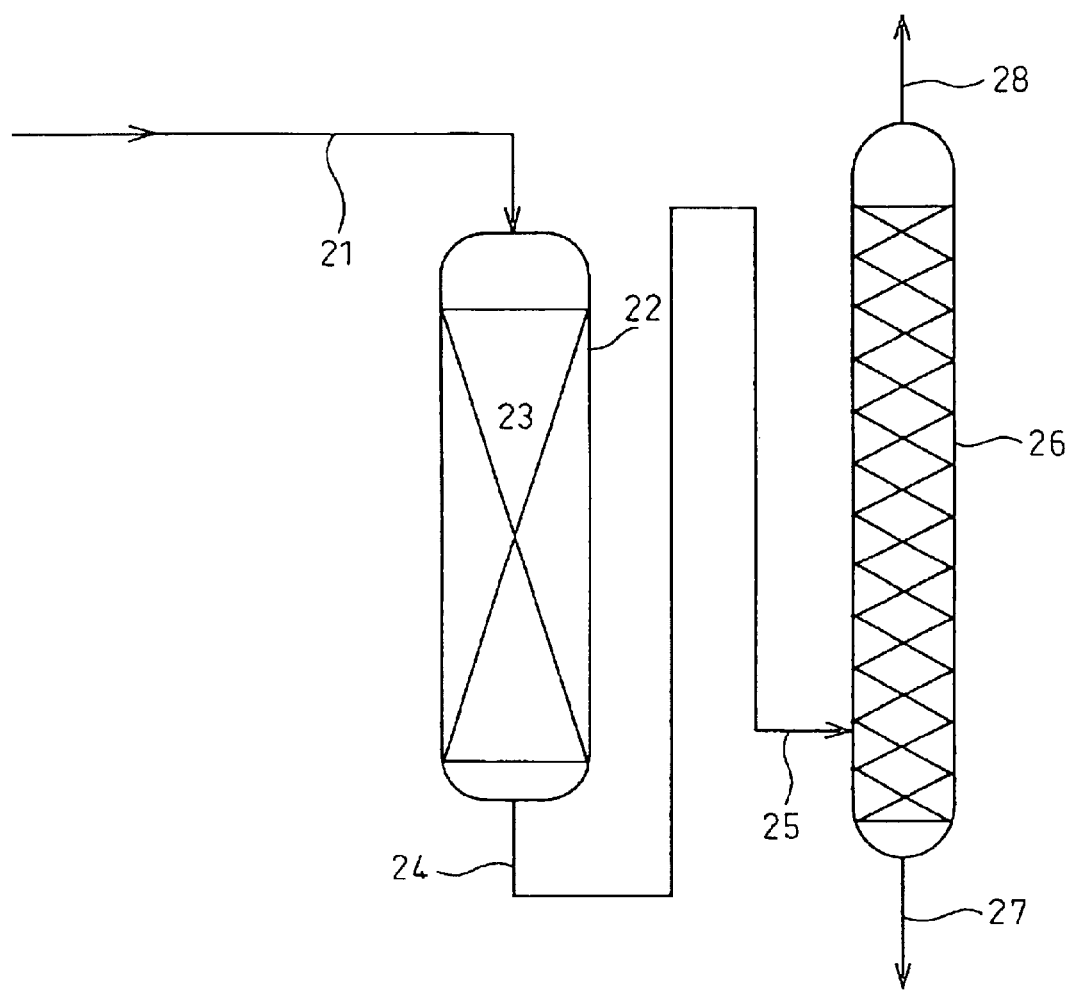
FIG. 2 is a flow sheet showing an embodiment of the apparatus system for the treatment with an ion exchange resin used in Example according to the present invention.

The resultant reaction product gas was cooled so as to be separated into a non-condensed component and a condensed component, and water was added to the condensed component so as to provide a volume ratio of 1:1. The resultant mixture was circulated with a space velocity of 1/hr (i.e., 500 ml/hr) as shown in FIG. 2, by using 500 ml of an acidic ion-exchange resin (trade name: Dia Ion SK-104H, mfd. by Mitsubishi Chemical K.K.). In this manner, a portion of the allyl acetate was converted into allyl alcohol, and after the hydrolysis reaction, the crude reaction product liquid was distilled to obtain a composition comprising allyl alcohol, allyl acetate and water as main components from the top of the column.

The composition comprising allyl alcohol, allyl acetate and water as main components which had been obtained from the top of the column was cooled so as to be phase-separated into an oily phase and an aqueous phase, and the following composition (hereinafter, referred to as "Composition-C") was obtained from the oily phase.

| Composition-C |
| --- |
| Allyl acetate 97.1 wt. % |
| Allyl alcohol 0.5 wt. % |
| Acetic acid 2.0 wt. % |
| Water content 0.2 wt. % |
| Others 0.2 wt. % |

500 ml of activated alumina (trade name: Tomita-A61, mfd. by Tomita Pharmaceutical K.K.) was packed into a reactor made of glass having a diameter of 100 mm, and the Composition-C was circulated therein so as to provide a space velocity of 1/hr (i.e., 500 ml/hr), to thereby obtain a mixture having the following composition (hereinafter, referred to as "Composition-D").

| Composition-D |
| --- |
| Allyl acetate 99.2 wt. % |
| Allyl alcohol 0.4 wt. % |
| Acetic acid 0.2 wt. % |
| Water content 0.1 wt. % |
| Others 0.1 wt. % |

(Hydrogenation of Allyl Ester)

Referring to FIG. 1, 130 ml of a carrier-type rhodium catalyst (alumina carrier, pellet with diameter of 3 mm×length of 3 mm, rhodium content 0.5%, specific surface area 100 m²/g, mfd. by NE-Chem Cat K.K.) was packed into a cylinder-type reactor made of stainless steel equipped with a jacket and having an inside diameter of 20 mmφ, the jacket temperature was set to 90.0° C., and the pressure in the reactor was adjusted to 1.0 MPa (gauge pressure) by use of hydrogen. From the upper part of the reactor, 10 kg of the Composition-D prepared above was charged thereinto and was circulated therein at 40° C. at a rate of 550 ml/hr, and hydrogen was also circulated in the reactor at a rate of 18.6 Nl/hr. The temperature of the reactor outlet (bottom portion of the catalyst layer) was 90.50C.

The reaction mixture from the reactor outlet was condensed to obtain 10 kg of a liquid. The resultant liquid was analyzed by using gas chromatography under the above-mentioned conditions (except that the injection temperature was 200° C.), and it was found that the conversion of allyl acetate was 100.0%, the selectivity factor for n-propyl acetate was 99.1%, the yield of n-propyl acetate was 99.1%, and the selectivity factor for acetic acid was 0.8%.

Example 3A-3

Referring to FIG. 1, 130 ml of a carrier-type ruthenium catalyst (alumina carrier, pellet with diameter of 3 mm×length of 3 mm, ruthenium content 0.5%, specific surface area 100 m$^2$/g, mfd. by NE-Chem Cat K.K.) was packed into a cylinder-type reactor made of stainless steel equipped with a jacket and having an inside diameter of 20 mm$\phi$, the jacket temperature was set to 90.0° C., and the pressure in the reactor was adjusted to 2.0 MPa (gauge pressure) by use of hydrogen. From the upper part of the reactor, 10 kg of the Composition-B prepared above was charged thereinto and was circulated therein at 40° C. at a rate of 550 ml/hr, and hydrogen was also circulated in the reactor at a rate of 18.6 Nl/hr. The temperature of the reactor outlet (bottom portion of the catalyst layer) was 90.5° C.

The reaction mixture from the reactor outlet was condensed to obtain 10 kg of a liquid. The resultant liquid was analyzed by using gas chromatography under the above-mentioned conditions (except that the injection temperature was 200° C.), and it was found that the conversion of allyl acetate was 99.8%, the selectivity factor for n-propyl acetate was 99.0%, the yield of n-propyl acetate was 98.8%, and the selectivity factor for acetic acid was 0.9%.

Example 3A-4

One liter of a catalyst having a particle size of 5 mm was obtained through an impregnation method by causing 4.5 g of palladium and 52 g of potassium acetate to be carried on 540 g of silica (surface area 96 m$^2$/g, pore volume 0.78 ml/g, average pore radius 15 nm, bulk density 540 g/l). One liter of the thus obtained catalyst was packed into a reactor made of stainless steel having a diameter of 27 mm. The gas to be charged thereinto was adjusted so as to provide a gas composition comprising 12 mol % of isobutene, 7.5 mol % of oxygen, 9 mol % of acetic acid, and 71.5 mol % of a diluting gas, and the gas was supplied onto the catalyst which had been heated to 145° C. so as to provide a space velocity of 1800/hr and to cause a reaction at a reaction pressure of 0.4 MPa (gauge pressure).

The resultant reaction product gas was cooled so as to be separated into a non-condensed component and a condensed component, and the crude reaction product liquid was distilled to obtain the following composition (hereinafter, referred to as "Composition-E") from the top portion of the column.

| Composition-E |
| --- |
| Methallyl acetate 97.7 wt. % |
| Allyl alcohol 0.1 wt. % |
| Acetic acid 2.0 wt. % |
| Others 0.2 wt. % |

500 ml of activated alumina (trade name: Tomita-A61, mfd. by Tomita Pharmaceutical K.K.) was packed into a reactor made of glass having a diameter of 100 mm, and the Composition-E prepared above was circulated therein so as to provide a space velocity of 1/hr (i.e., 500 ml/hr), to thereby obtain a mixture having the following composition (hereinafter, referred to as "Composition-F").

| Composition-F |
| --- |
| Methallyl acetate 99.6 wt. % |
| Allyl alcohol 0.1 wt. % |
| Acetic acid 0.1 wt. % |
| Others 0.2 wt. % |

Referring to FIG. 1, 130 ml of a carrier-type palladium catalyst (alumina carrier, pellet with diameter of 3 mm×length of 3 mm, palladium content 0.3%, specific surface area 100 m$^2$/g, mfd. by NE-Chem Cat K.K.) was packed into a cylinder-type reactor made of stainless steel equipped with a jacket and having an inside diameter of 20 mm$\phi$, the jacket temperature was set to 90.0° C., and the pressure in the reactor was adjusted to 1.0 MPa (gauge pressure) by use of hydrogen. From the upper part of the reactor, 10 kg of the Composition-F prepared above was charged thereinto and was circulated therein at 40° C. at a rate of 550 ml/hr, and hydrogen was also circulated in the reactor at a rate of 18.6 Nl/hr. The temperature of the reactor outlet (bottom portion of the catalyst layer) was 90.5° C.

The reaction mixture from the reactor outlet was condensed to obtain 10 kg of a liquid. The resultant liquid was analyzed by using gas chromatography under the above-mentioned conditions (except that the injection temperature was 200° C.), and it was found that the conversion of methallyl acetate was 100.0%, the selectivity factor for isobutyl acetate was 99.0%, the yield of isobutyl acetate was 99.0%, and the selectivity factor for acetic acid was 0.8%.

Example 3B-1

Referring to FIG. 1, 130 ml of a carrier-type palladium catalyst (alumina carrier, pellet with diameter of 3 mm×length of 3 mm, palladium content 0.3%, specific surface area 100 m$^2$/g, mfd. by NE-Chem Cat K.K.) was packed into a cylinder-type reactor made of stainless steel equipped with a jacket and having an inside diameter of 20 mm$\phi$, the jacket temperature was set to 90.0° C., and the pressure in the reactor was adjusted to 1.0 MPa (gauge pressure) by use of hydrogen. From the upper part of the reactor, 10 kg of the Composition-A (containing 2.0 wt. % of acetic acid) was charged thereinto and was circulated therein at 40° C. at a rate of 550 ml/hr, and hydrogen was also circulated in the reactor at a rate of 18.6 Nl/hr. The temperature of the reactor outlet (bottom portion of the catalyst layer) was 90.5° C.

The reaction mixture from the reactor outlet was condensed to obtain 10 kg of a reaction product liquid. The resultant liquid was analyzed by using gas chromatography, and it was found that the conversion of allyl acetate was 99.9%, the selectivity factor for n-propyl acetate was 97.0%, the yield of n-propyl acetate was 96.9%, and the selectivity factor for acetic acid was 2.9%.

Example 3B-2

Referring to FIG. 1, 130 ml of a carrier-type rhodium catalyst (alumina carrier, pellet with diameter of 3 mm×length of 3 mm, rhodium content 0.3%, specific surface area 100 m$^2$/g, mfd. by NE-Chem Cat K.K.) was packed into a cylinder-type reactor made of stainless steel equipped with a jacket and having an inside diameter of 20 mmφ, the jacket temperature was set to 90.0° C., and the pressure in the reactor was adjusted to 1.0 MPa (gauge pressure) by use of hydrogen. From the upper part of the reactor, 10 kg of the Composition-C (containing 2.0 wt. % of acetic acid) was charged thereinto and was circulated therein at 40° C. at a rate of 550 ml/hr, and hydrogen was also circulated in the reactor at a rate of 18.6 Nl/hr. The temperature of the reactor outlet (bottom portion of the catalyst layer) was 90.5° C.

The reaction mixture from the reactor outlet was condensed to obtain 10 kg of a liquid. The resultant liquid was analyzed by using gas chromatography, and it was found that the conversion of allyl acetate was 99.9%, the selectivity factor for n-propyl acetate was 97.0%, the yield of n-propyl acetate was 96.9%, and the selectivity factor for acetic acid was 2.9%.

Example 3B-3

Referring to FIG. 1., 130 ml of a carrier-type ruthenium catalyst (alumina carrier, pellet with diameter of 3 mm×length of 3 mm, ruthenium content 0.5%, specific surface area 100 m$^2$/g, mfd. by NE-Chem Cat K.K.) was packed into a cylinder-type reactor made of stainless steel equipped with a jacket and having an inside diameter of 20 mmφ, the jacket temperature was set to 90.0° C., and the pressure in the reactor was adjusted to 1.0 MPa (gauge pressure) by use of hydrogen. From the upper part of the reactor, 10 kg of the Composition-A (containing 2.0 wt. % of acetic acid) was charged thereinto and was circulated therein at 40° C. at a rate of 550 ml/hr, and hydrogen was also circulated in the reactor at a rate of 18.6 Nl/hr. The temperature of the reactor outlet (bottom portion of the catalyst layer) was 90.5° C.

The reaction mixture from the reactor outlet was condensed to obtain 10 kg of a liquid. The resultant liquid was analyzed by using gas chromatography, and it was found that the conversion of allyl acetate was 99.7%, the selectivity factor for n-propyl acetate was 97.0%, the yield of n-propyl acetate was 96.7%, and the selectivity factor for acetic acid was 2.9%.

Example 3B-4

Referring to FIG. 1, 130 ml of a carrier-type palladium catalyst (alumina carrier, pellet with diameter of 3 mm×length of 3 mm, palladium content 0.3%, specific surface area 100 m$^2$/g, mfd. by NE-Chem Cat K.K.) was packed into a cylinder-type reactor made of stainless steel equipped with a jacket and having an inside diameter of 20 mmφ, the jacket temperature was set to 90.0° C., and the pressure in the reactor was adjusted to 1.0 MPa (gauge pressure) by use of hydrogen. From the upper part of the reactor, 10 kg of the Composition-E (containing 2.0 wt. % of acetic acid) was charged thereinto and was circulated therein at 40° C. at a rate of 550 ml/hr, and hydrogen was also circulated in the reactor at a rate of 18.6 Nl/hr. The temperature of the reactor outlet (bottom portion of the catalyst layer) was 90.5° C.

The reaction mixture from the reactor outlet was condensed to obtain 10 kg of a liquid. The resultant liquid was analyzed by using gas chromatography, and it was found that the conversion of methallyl acetate was 99.9%, the selectivity factor for isobutyl acetate was 97.0%, the yield of isobutyl acetate was 96.9%, and the selectivity factor for acetic acid was 2.9%.

As described above, based on the comparison between Example 1 and Comparative Example 1, Example 2 and Comparative Example 2, Example 3 and Comparative Example 3, and Example 4 and Comparative Example 4, it may be understood that the production process according to the present invention suppresses the hydrogenolysis reaction and as a result it can provide the corresponding hydrogenated ester with a high yield.

Industrial Applicability

As described hereinabove, according to the present invention, a hydrogenated ester (particularly, a saturated ester) can be industrially produced while maintaining the resultant raw material conversion, selectivity factor, and yield to a high level. In the present invention, a complicated reaction apparatus or reaction process is not necessarily required.

According to an embodiment of the present invention, saturated esters can be industrially produced at a low cost by conducting a hydrogenation reaction in a liquid phase by use of a hydrogenating catalyst commonly used, and by use of a raw material liquid which has been obtained by diluting an unsaturated group-containing ester with a solvent inert to the hydrogenation reaction.

According to another embodiment of the present invention, an unsaturated group-containing ester represented by the general formula (1) is hydrogenated in the presence of a specific catalyst, i.e., a hydrogenating catalyst having an acidity of $1.0 \times 10^{-1}$ mmol/g or less as measured by the ammonia-TPD method and containing at least one metal selected from the group consisting of Group 8 elements, Group 9 elements, and Group 10 elements in the periodic table, whereby the amount of carboxylic acid generated by the hydrogenolysis can be decreased extremely, and the unsaturated group-containing ester can be converted into a hydrogenated ester at a high conversion rate and with a high yield.

According to a further embodiment of the present invention, an ally-type ester is hydrogenated by using a hydrogenating catalyst so as to obtain a hydrogenated ester corresponding to the allyl-type ester, wherein the concentration of a carboxylic acid in the raw material containing the allyl-type ester is made 1 wt. % or less, whereby the hydrogenolysis reaction it can be suppressed and the hydrogenated ester can be provided with a high yield. In such a manner, the hydrogenated ester can be produced industrially advantageously.

What is claimed is:

1. A process for producing a hydrogenated ester by hydrogenating an unsaturated group-containing ester represented by formula (3) by using a hydrogenating catalyst wherein the hydrogenating catalyst is a compound comprising at least one element selected from the group consisting of Group 8 elements, Group 9 elements and Group 10 elements in the periodic table a according to Nomenclature of Inorganic Chemistry, Revised Edition, 1989, International Union of Pure and Applied Chemistry, so as to produce a hydrogenated ester corresponding to the unsaturated group-containing ester, wherein the concentration of a carboxylic acid in a raw material containing the unsaturated group-containing ester represented by formula (3) is 1 wt. % or less:

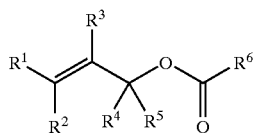

(3)

wherein $R^1$, $R^2$, $R^3$, $R^4$ and $R^5$ denote an arbitrary alkyl group containing 1–10 carbon atoms, a arbitrary alkenyl group containing 2–10 carbon atoms, or a hydrogen atom and may be the same as or different from each other; the alkyl group and alkenyl group may be either straight-chain or branched; $R^6$ represents a C1–C10 alkyl group.

2. The process for producing a hydrogenated ester according to claim 1, wherein the hydrogenating catalyst comprises at least one element selected from the group consisting of palladium, rhodium or ruthenium.

3. The process for producing a hydrogenated ester according to claim 1, wherein the allyl-type ester represented by formula (1) is at least one allyl-type ester selected from the group consisting of allyl acetate, crotyl acetate, methallyl acetate, allyl propionate, crotyl propionate, and methallyl propionate.

4. A process for producing a hydrogenated ester by hydrogenating an unsaturated group-containing ester represented by the following formula (1) in the presence of a hydrogenating catalyst wherein the hydrogenation catalyst is a compound comprising at least one element selected from the group consisting of Group 8 elements, Group 9 elements and Group 10 elements according to Nomenclature of Inorganic Chemistry, Revised Edition, 1989, International Union of Pure and Applied Chemistry, so as to produce the corresponding hydrogenated ester corresponding to the unsaturated group-containing ester

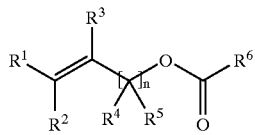

(1)

wherein $R^1$, $R^2$, $R^3$, $R^4$ and $R^5$ denote an arbitrary alkyl group containing 1–10 carbon atoms, an arbitrary alkenyl group containing 2–10 carbon atoms, or a hydrogen atom and may be the same as or different from each other; the alkyl group and alkenyl group may be either straight-chain or branched; $R^6$ denotes an arbitrary alkyl group which contains 1–10 carbon atoms and may be either straight-chain or branched; and n is 0 or 1, comprising providing an unsaturated group-containing ester represented by formula (1), wherein the concentration of the unsaturated group-containing ester represented by formula (1) at the initial time of the hydrogenation reaction thereof is in the range of 1 wt %–50 wt % based on the entirety of the raw material liquid containing the unsaturated group-containing ester; and reacting the unsaturated group-containing ester with hydrogen while diluting said unsaturated group-containing ester with an inert solvent to effectuate a hydrogenation reaction, wherein the inert solvent is the corresponding hydrogenated ester.

5. The process for producing a hydrogenated ester according to claim 4, wherein the corresponding hydrogenated ester is a portion or the entirety of the recycled hydrogenated ester which has been produced by the hydrogenation reaction of the unsaturated group-containing ester represented by formula (1).

6. The process for producing a hydrogenated ester according to claim 4, wherein the reaction temperature at the initial time of the hydrogenation reaction is in the range of 0° C. to 200° C.

7. The process for producing a hydrogenated ester according to claim 4, wherein the unsaturated group-containing ester represented by formula (1) is at least one compound selected from the group consisting of allyl acetate, crotyl acetate, methallyl acetate, allyl propionate, crotyl propionate, methallyl propionate, vinyl acetate, vinyl propionate, 1,3-butadienyl acetate, and 1,3-butadienyl propionate.

8. The process for producing a hydrogenated ester according to claim 4, wherein the hydrogenation reaction is conducted by a liquid-phase reaction by use of a fixed bed-type reactor.

9. A process for producing a hydrogenated ester, wherein an unsaturated group-containing ester represented by formula (1) is hydrogenated by using a hydrogenating catalyst wherein the hydrogenating catalyst is a compound comprising at least one element selected from the group consisting of Group 8 elements, Group 9 elements, and Group 10 elements in the periodic table according to Nomenclature of Inorganic Chemistry, Revised Edition, 1989, International Union of Pure and Applied Chemistry, and is to be used for hydrogenating an unsaturated group-containing ester represented by the following formula (1) to thereby produce a hydrogenated ester represented by the following formula (2), wherein the catalyst has an acidity of $1.0 \times 10^{-1}$ mol/g or less:

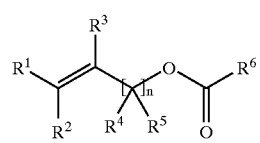

(1)

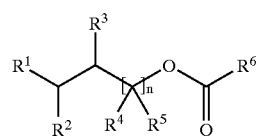

(2)

wherein n represents 0 or 1; $R^1$, $R^2$, $R^3$, $R^4$ and $R^5$ denote an arbitrary alkyl group containing 1–10 carbon atoms, an arbitrary alkenyl group containing 2–10 carbon atoms, or a hydrogen atom and may be the same as or different from each other; the alkyl group and alkenyl group may be either straight-chain or branched; and $R^6$ represents a $C_1$–$C_{10}$ alkyl group.

10. The process for producing a hydrogenated ester according to claim 9, wherein the hydrogenation is carried out at a reaction temperature in the range of 0° to 200° C.

11. The process for producing a hydrogenated ester according to claim 10, wherein the inert solvent is a hydrogenated ester corresponding to the unsaturated group-containing ester as a raw material.

12. The process for producing a hydrogenated ester according to claim 9, wherein the unsaturated group-containing ester as a raw material is diluted with an inert solvent and the resultant diluted liquid is used as the raw material-containing liquid to be hydrogenated.

13. The process for producing a hydrogenated ester according to claim 9, wherein the hydrogenating catalyst comprises at least one element selected from the group consisting of palladium, ruthenium and rhodium.

14. A process for producing a hydrogenated ester, wherein at least one unsaturated group-containing ester selected from the group consisting of allyl acetate, crotyl acetate, methallyl acetate, allyl propionate, crotyl propionate, methallyl propionate, vinyl acetate, 1,3-butadienyl acetate, 1-methyl-1-propenyl acetate, vinyl propionate, 1,3-butadienyl propionate, and 1-methyl-1-propenyl propionate is hydrogenated by using a hydrogenating catalyst wherein the hydrogenating catalyst is a compound comprising at least one element selected from the group consisting of Group 8 elements, Group 9 elements, and Group 10 elements in the periodic table according to Nomenclature of Inorganic Chemistry, Revised Edition, 1989, International Union of Pure and Applied Chemistry, and is to be used for hydrogenating an unsaturated group-containing ester represented by the following formula (1) to thereby produce a hydrogenated ester represented by the following formula (2), wherein the catalyst has an acidity of $1.0 \times 10^{-1}$ mol/g or less:

(1)

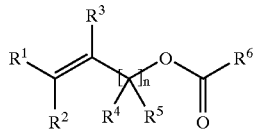

-continued (2)

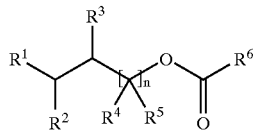

wherein n represents 0 or 1; $R^1$, $R^2$, $R^3$, $R^4$ and $R^5$ denote an arbitrary alkyl group containing 1–10 carbon atoms, an arbitrary alkenyl group containing 2–10 carbon atoms, or a hydrogen atom and may be the same as or different from each other; the alkyl group and alkenyl group may be either straight-chain or branched; and $R^6$ represents a $C_1$–$C_{10}$ alkyl group.

15. The process for producing a hydrogenated ester according to claim 14, wherein the hydrogenation is carried out at a reaction temperature in the range of 0° to 200° C.

16. The process for producing a hydrogenated ester according to claim 15, wherein the inert solvent is a hydrogenated ester corresponding to the unsaturated group-containing ester as a raw material.

17. The process for producing a hydrogenated ester according to claim 14, wherein the unsaturated group-containing ester as a raw material is diluted with an inert solvent and the resultant diluted liquid is used as the raw material-containing liquid to be hydrogenated.

18. The process for producing a hydrogenated ester according to claim 14, wherein the hydrogenating catalyst comprises at least one element selected from the group consisting of palladium, ruthenium and rhodium.

* * * * *